US012698497B2

(12) United States Patent
Weltz et al.

(10) Patent No.: US 12,698,497 B2
(45) Date of Patent: Aug. 4, 2026

(54) STABILITY AND ACTIVITY OF ENZYMES BY IMMOBILIZATION

(71) Applicant: The Regents of the University of Colorado, Denver, CO (US)

(72) Inventors: James S. Weltz, Denver, CO (US); Joel L. Kaar, Lafayette, CO (US); Daniel K. Schwartz, Boulder, CO (US); Hector Sanchez-Moran, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 559 days.

(21) Appl. No.: 18/036,678

(22) PCT Filed: Nov. 15, 2021

(86) PCT No.: PCT/US2021/072409
§ 371 (c)(1),
(2) Date: May 12, 2023

(87) PCT Pub. No.: WO2022/104385
PCT Pub. Date: May 19, 2022

(65) Prior Publication Data
US 2024/0026333 A1 Jan. 25, 2024

Related U.S. Application Data

(60) Provisional application No. 63/113,234, filed on Nov. 13, 2020.

(51) Int. Cl.
*C12N 11/08* (2020.01)
*B01J 13/14* (2006.01)
*C12N 9/20* (2006.01)

(52) U.S. Cl.
CPC .............. *C12N 11/08* (2013.01); *B01J 13/14* (2013.01); *C12N 9/20* (2013.01)

(58) Field of Classification Search
CPC . C12N 11/08; C12N 9/20; B01J 13/14; Y02P 20/50; Y02P 20/52; Y02P 20/584
See application file for complete search history.

(56) References Cited

U.S. PATENT DOCUMENTS

| | | |
|---|---|---|
| 6,403,706 B1 | 6/2002 | Wang et al. |
| 6,692,914 B1 | 2/2004 | Klaerner et al. |
| 9,535,062 B2 | 1/2017 | Jiang et al. |
| 9,598,544 B2 | 3/2017 | Jiang et al. |
| 10,031,138 B2 | 7/2018 | Jiang et al. |
| 2004/0101741 A1 | 5/2004 | Minteer et al. |
| 2007/0111289 A1 | 5/2007 | Yang et al. |
| 2008/0139399 A1 | 6/2008 | Fonnum et al. |
| 2010/0041123 A1 | 2/2010 | Minteer et al. |
| 2010/0196985 A1 | 8/2010 | Hotchkiss et al. |
| 2016/0015869 A1 | 1/2016 | Omata et al. |
| 2016/0244741 A1 | 8/2016 | Russell et al. |
| 2017/0342211 A1 | 11/2017 | Fomina et al. |
| 2017/0355968 A1 | 12/2017 | Nazor et al. |
| 2019/0231703 A1 | 8/2019 | Liang |
| 2020/0061597 A1 | 2/2020 | Corgie et al. |
| 2021/0198516 A1 | 7/2021 | Locklin et al. |

FOREIGN PATENT DOCUMENTS

| | | | |
|---|---|---|---|
| CA | 2928121 A1 | 10/2017 | |
| CN | 110183710 A * | 8/2019 | ............... C08J 7/16 |
| EP | 0233524 A2 | 8/1987 | |
| JP | 2009100673 A | 5/2009 | |

OTHER PUBLICATIONS

Koening (Koening et al, In-situ-Investigation of Enzyme Immobilization on Polymer Brushes, 2019, 7, 101, p. 1-8).*
Weltz (Weltz et al, Dramatic increase in catalytic performance of immobilized lipases by their stabilization on polymer brush support, ACS Catalysis, 2019, 9, 4992-5001).*
Weltz JS, Kienle DF, Schwartz DK, Kaar JL. Reduced Enzyme Dynamics upon Multipoint Covalent Immobilization Leads to Stability-Activity Trade-off. J Am Chem Soc. Feb. 19, 2020;142(7):3463-3471. doi: 10.1021/jacs.9b11707. Epub Feb. 10, 2020. PMID: 31986020.
James S. Weltz, Daniel F. Kienle, Daniel K. Schwartz, and Joel L. Kaar, ACS Catalysis 2019 9 (6), 4992-5001 DOI: 10.1021/acscatal.9b01176.
Jiang H, Xu FJ. Biomolecule-functionalized polymer brushes. Chem Soc Rev. Apr. 21, 2013;42(8):3394-426. doi: 10.1039/c2cs35453e. PMID: 23348574.
Bayramoglu G, Doz T, Ozalp VC, Arica MY. Improvement stability and performance of invertase via immobilization on to silanized and polymer brush grafted magnetic nanoparticles. Food Chem. Apr. 15, 2017;221:1442-1450. doi: 10.1016/j.foodchem.2016.11.007. Epub Nov. 2, 2016. PMID: 27979113.
Liqian Zhang, Yan Sun, Poly(carboxybetaine methacrylate)-grafted silica nanoparticle: A novel carrier for enzyme immobilization, Biochemical Engineering Journal, vol. 132, 2018, pp. 122-129, ISSN 1369-703X, https://doi.org/10.1016/j.bej.2018.01.013.
(Continued)

*Primary Examiner* — Kumar R Bhushan
(74) *Attorney, Agent, or Firm* — McGaw Law, P.C.; Michael M. McGaw

(57) ABSTRACT

A polymer brush composed of statistical copolymers of hydrophilic and hydrophobic monomers for enzyme immobilization. The heterogeneous polymer brushes stabilized four different lipases against high temperatures. Notably, the statistical copolymers stabilized the four lipases to a greater extent than a homopolymer brush. Additionally, in the case of *Rhizomucor miehei* lipase, statistical copolymers stabilized the enzyme to a greater extent than homopolymers of either hydrophilic or hydrophobic monomers. The resulting increase in high-temperature stability enabled significant improvements in catalytic rates by operating reactions at elevated temperatures, which is desirable for enzyme catalysis and sensing applications. Additionally, stabilization against elevated temperatures implies stabilization against non-aqueous solvents, which is of critical importance to numerous applications of biocatalysts.

10 Claims, 11 Drawing Sheets

(56)　　　　　References Cited

OTHER PUBLICATIONS

Alice Rosenthal, Sebastian Rauch, Klaus-Jochen Eichhorn, Manfred Stamm, Petra Uhlmann, Enzyme immobilization on protein-resistant PNIPAAm brushes: impact of biotin linker length on enzyme amount and catalytic activity, Colloids and Surfaces B: Biointerfaces, vol. 171, 2018, pp. 351-357, ISSN 0927-7765, https://doi.org/10.1016/j.colsurfb.2018.07.047.

Hu Y, Liang B, Fang L, Ma G, Yang G, Zhu Q, Chen S, Ye X. Antifouling Zwitterionic Coating via Electrochemically Mediated Atom Transfer Radical Polymerization on Enzyme-Based Glucose Sensors for Long-Time Stability in 37 Serum. Langmuir. Nov. 15, 2016;32(45):11763-11770. doi: 10.1021/acs.langmuir.6b03016. Epub Nov. 3, 2016. PMID: 27756132.

Marschelke C, Muller M, Kopke D, Matura A, Sallat M, Synytska A. Hairy Particles with Immobilized Enzymes: Impact of Particle Topology on the Catalytic Activity. ACS Appl Mater Interfaces. Jan. 9, 2019;11(1):1645-1654. doi: 10.1021/acsami.8b17703. Epub Dec. 19, 2018. PMID: 30525381.

Koenig M, Konig U, Eichhorn KJ, Muller M, Stamm M, Uhlmann P. In-situ-Investigation of Enzyme Immobilization on Polymer Brushes. Front Chem. Mar. 7, 2019;7:101. doi: 10.3389/fchem.2019.00101. PMID: 30899756; PMCID: PMC6416228.

Sanchez-Moran, H., Weltz, U.S., Schwartz, D.K. and Kaar, J.L., 2021. Understanding design rules for optimizing the interface between immobilized enzymes and random copolymer brushes. ACS Applied Materials & Interfaces, 13(23), pp. 26694-26703.

Sanchez-Moran, H., Gonçalves, L.R.B., Schwartz, D.K. and Kaar, J.L., 2023. Framework for Optimizing Polymeric Supports for Immobilized Biocatalysts by Computational Analysis of Enzyme Surface Hydrophobicity. ACS Catalysis, 13(7), pp. 4304-4315.

Sánchez-Morán, H., Kaar, J.L. and Schwartz, D.K., 2024. Combinatorial High-Throughput Screening of Complex Polymeric Enzyme Immobilization Supports. Journal of the American Chemical Society, 146(13), pp. 9112-9123.

Sánchez-Morán, H., Kaar, J.L. and Schwartz, D.K., 2024. Supra-biological performance of immobilized enzymes enabled by chaperone-like specific non-covalent interactions. Nature Communications, 15(1), p. 2299.

Gauthier, M.A., Gibson, M.I. and Klok, H.A., 2009. Synthesis of functional polymers by post-polymerization modification. Angewandte Chemie International Edition, 48(1), pp. 48-58.

Barbey, R. and Klok, H.A., 2010. Room temperature, aqueous post-polymerization modification of glycidyl methacrylate-containing polymer brushes prepared via surface-initiated atom transfer radical polymerization. Langmuir, 26(23), pp. 18219-18230.

Zhang, M. and Muller, A.H.E. (2005), Cylindrical polymer brushes. J. Polym. Sci. A Polym. Chem., 43: 3461-3481. https://doi.org/10.1002/pola.20900.

Faulón Marruecos D, Saleh LS, Kim HH, Bryant SJ, Schwartz DK, Kaar JL. Stabilization of Fibronectin by Random Copolymer Brushes Inhibits Macrophage Activation. ACS Appl Bio Mater. Nov. 18, 2019;2(11):4698-4702. doi: 10.1021/acsabm.9b00815. Epub Nov. 6, 2019. PMID: 35021468.

Sánchez-Morán H, Weltz JS, Schwartz DK, Kaar JL. Understanding Design Rules for Optimizing the Interface between Immobilized Enzymes and Random Copolymer Brushes. ACS Appl Mater Interfaces. Jun. 16, 2021;13(23):26694-26703. doi: 10.1021/acsami.1c02443. Epub Jun. 3, 2021. PMID: 34081428.

Weltz, James & Kienle, Daniel & Schwartz, Daniel & Kaar, Joel. (2019). Dramatic Increase in Catalytic Performance of Immobilized Lipases by Their Stabilization on Polymer Brush Supports. ACS Catalysis. 9. 10.1021/acscatal.9b01176.

* cited by examiner

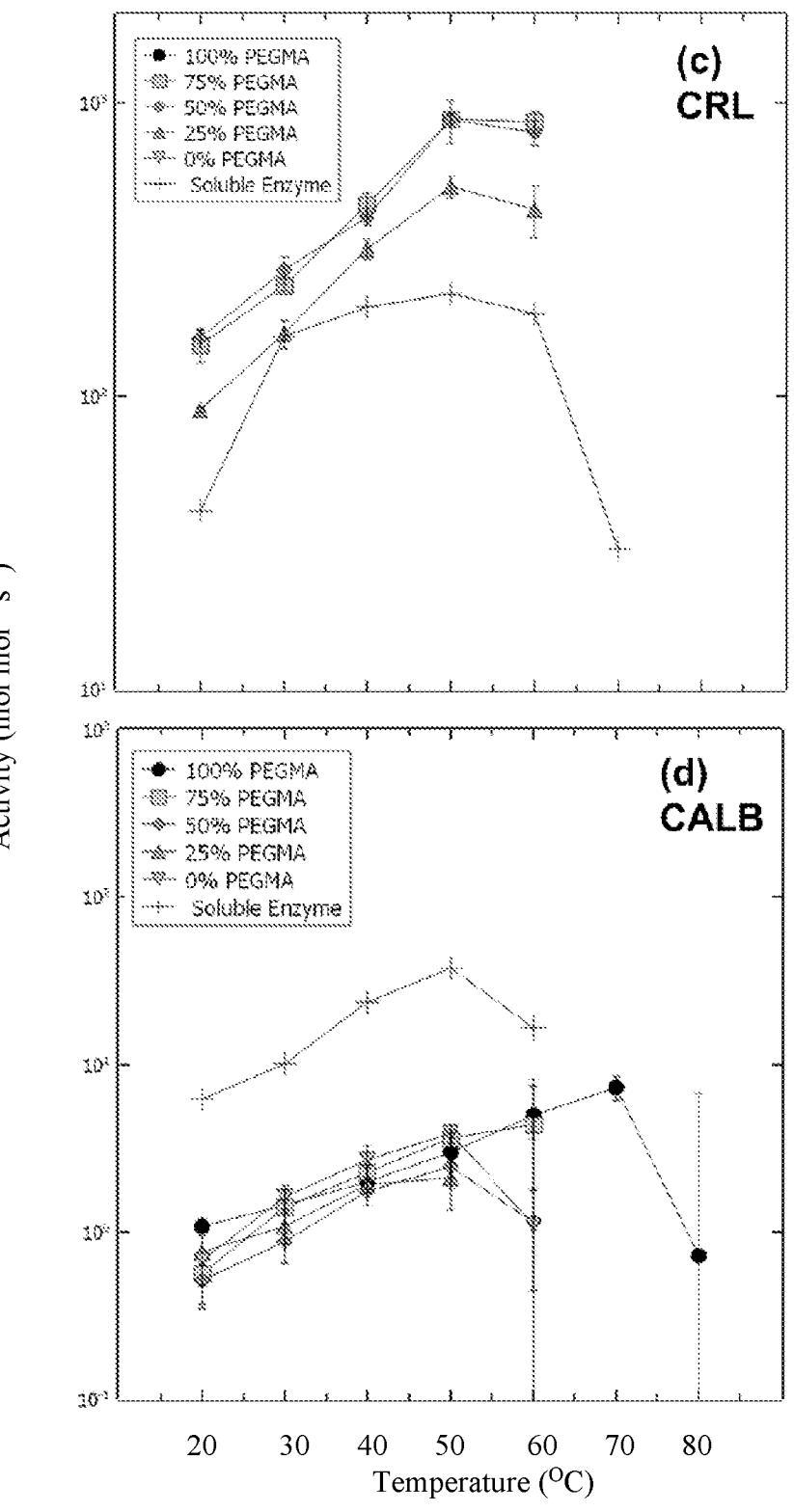
*FIG. 1 - continued* e
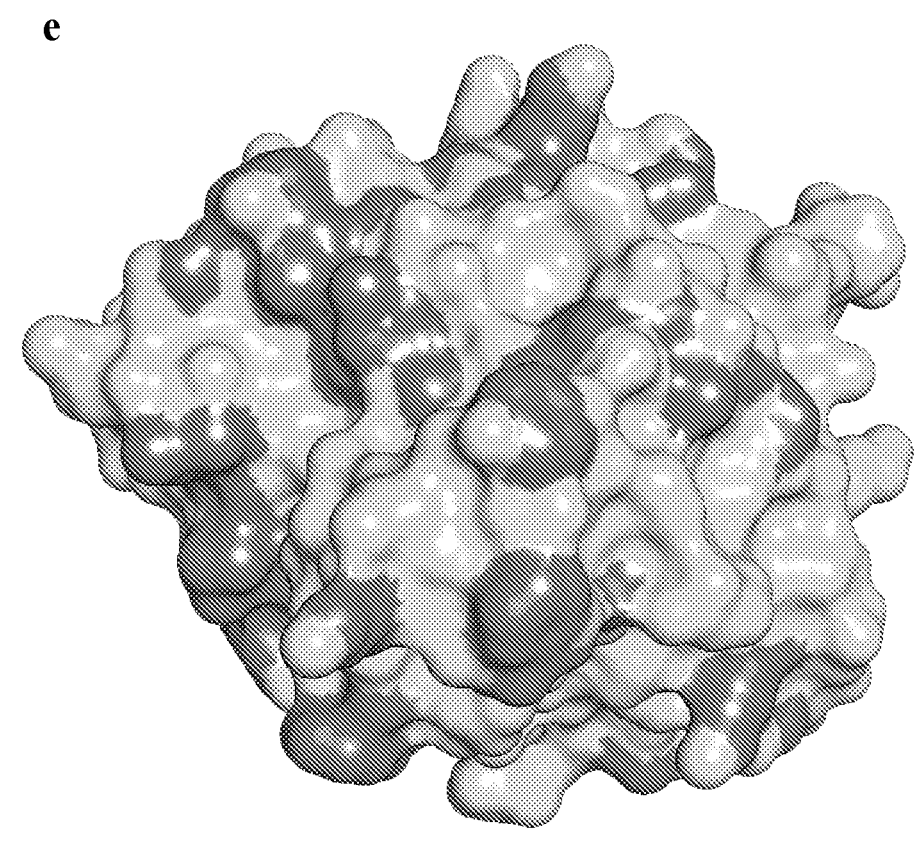
*FIG. 3 – continued*

*Bacillus Subtilis*
Lipase A
(LipA)

*Rhizomucor Miehei*
Lipase
(RML)

*Candida Rugosa*
Lipase
(CRL)

*Candida Antarctica*
Lipase
(CALB)

STABILITY AND ACTIVITY OF ENZYMES BY IMMOBILIZATION

CROSS-REFERENCE TO RELATED APPLICATIONS

This application claims the benefit of U.S. Provisional Application No. 63/113,234 filed Nov. 13, 2020.

STATEMENT OF GOVERNMENT INTEREST

This invention was made with government support under grant number W911NF-15-1-0141 awarded by the U.S. Army Research Office, and grant number HDTRA1-16-1-0045 awarded by DOD/DTRA. The government has certain rights in the invention.

FIELD OF INVENTION

This invention relates to methods and compositions for the catalytic enhancement of immobilized enzymes by tunable polymer materials.

BACKGROUND OF THE INVENTION

Enzymes are extraordinary catalysts with exquisite selectivity and activity under mild conditions and are, therefore, of increasing importance as catalysts. [Schmid, A., et al., Industrial Biocatalysis Today and Tomorrow. *Nature* 2001, 409 (January), 258-268; Campos, K. R. et al., The Importance of Synthetic Chemistry in the Pharmaceutical Industry. *Science* (80-.). 2019, 363 (6424); Bornscheuer, U. T., et al., Engineering the Third Wave of Biocatalysis. *Nature* 2012, 485 (7397), 185-194.] However, enzymes are only marginally stable, and small changes in environmental conditions, including temperature, pH, and solvent, cause rapid inactivation. [Taverna, D. M., et al., Why Are Proteins Marginally Stable? *Proteins Struct. Funct. Genet.* 2002, 46 (1), 105-109.] Therefore, stabilization of enzymes has been the focus of decades of research in order to broaden the scope of conditions under which enzymes are active, improve catalyst longevity, and increase catalytic rates by operating reactions at elevated temperatures. [Adams, M. W., et al., Extremozymes: Expanding the Limits of Biocatalysis. *Nature Biotechnology.* 1995, pp 662-668; Haki, G. D.; Rakshit, S. K. Developments in Industrially Important Thermostable Enzymes: A Review. *Bioresour. Technol.* 2003, 89 (1), 17-34; Devine, P. N., et al., Extending the Application of Biocatalysis to Meet the Challenges of Drug Development. *Nat. Rev. Chem.* 2018, 2 (12), 409-421.] In the case of enzyme catalysis, elevated temperatures typically are above ambient temperatures, but less than the boiling point of water (i.e., between 20° C. and 100° C.). It would be highly desirable and advantageous to have additional methods and compositions for the stabilization of enzymes. The present invention provides such compositions and methods as will become readily apparent in the following disclosure.

SUMMARY OF THE INVENTION

Enzyme stabilization can be achieved through immobilization. [Cao, L. Immobilised Enzymes: Science or Art? *Curr. Opin. Chem. Biol.* 2005, 9 (2), 217-226; Datta, S.; Christena, L. R.; Rajaram, Y. R. S. Enzyme Immobilization: An Overview on Techniques and Support Materials. 3 *Biotech* 2013, 3 (1), 1-9; Klibanov, A. M. Enzyme Stabilization by Immobilization. *Anal. Biochem.* 1979, 93, 1-25.]

Besides stabilization, enzyme immobilization also facilitates recycling of the expensive catalyst, reduces downstream separations, and makes them compatible with various biosensing modalities. [Barbosa, O., et al., Heterofunctional Supports in Enzyme Immobilization: From Traditional Immobilization Protocols to Opportunities in Tuning Enzyme Properties. *Biomacromolecules* 2013, 14 (8), 2433-2462; Barbosa, O., et al., Strategies for the One-Step Immobilization-Purification of Enzymes as Industrial Biocatalysts. *Biotechnol. Adv.* 2015, 33 (5), 435-456; Rodrigues, R. C., et al., Modifying Enzyme Activity and Selectivity by Immobilization. *Chem. Soc. Rev.* 2013, 42 (15), 6290-6307.] One approach to enzyme immobilization is the use of polymer brushes. Polymer brushes are surfaces decorated with a high density of polymers such that steric interactions cause the polymers to adopt an extended or brush-like, conformation relative to the solid surface, and can be generated by adsorbing or covalently attaching polymers to a surface ("grafted to") or by synthesizing polymers from an initiator functionalized surface ("grafted from"). [Brittain, W. J.; Minko, S. A Structural Definition of Polymer Brushes. *J. Polym. Sci. Part A Polym. Chem.* 2007, 45 (16), 3505-3512.] Polymer brushes are one approach to enzyme immobilization given the diversity of solid supports which can be functionalized with polymer brushes and the variety of polymer chemistries available. [Cullen, S. P., et al., Polymerie Brushes as Functional Templates for Immobilizing Ribonuclease A: Study of Binding Kinetics and Activity. *Langmuir* 2008, 24 (3), 913-920; Zoppe, J. O., et al., Surface-Initiated Controlled Radical Polymerization: State-of-the-Art, Opportunities, and Challenges in Surface and Interface Engineering with Polymer Brushes. *Chem. Rev.* 2017, 117 (3), 1105-1318; Xu, F. J., et al., Bioactive Surfaces and Biomaterials via Atom Transfer Radical Polymerization. *Prog. Polym. Sci.* 2009, 34 (8), 719-761.]

Polymer brush supports composed of hydrophobic monomers can be employed to improve enzyme loading by the strong hydrophobic driving force for enzyme adsorption. Alternatively, hydrophilic polymers can be employed because hydrophilic surfaces reduce surface-induced unfolding of the enzyme upon immobilization.

Enhanced enzyme stabilization is demonstrated herein by immobilization of enzymes to polymer brushes composed of statistical copolymers containing both hydrophilic and hydrophobic monomers. Surprisingly, all lipases assayed exhibited greater high temperature stability when immobilized to statistical copolymers compared to one of the homopolymers. In the case of *Candida rugosa* lipase (CRL), the statistical copolymers were more stabilizing than homopolymers of either composition. Importantly, this stability enabled operation of the enzyme at elevated temperatures, achieving significantly higher rates of catalysis. Additionally, high temperature stability suggests longer catalyst lifetimes and greater resistance to inactivation by organic solvents, which have significant benefits for industrial catalysis and biosensing. [Iyer, P. V.; Ananthanarayan, L. Enzyme Stability and Stabilization-Aqueous and Non-Aqueous Environment. *Process Biochem.* 2008, 43 (10), 1019-1032.]

Increasing enzyme stability through immobilization has been one approach to promote a boost to enzyme performance for industrial biocatalysis. However, increases in immobilized enzyme stability are typically enzyme specific and achieved by empirical, trial-and-error endeavors. In this work, a novel machine learning-based computational technique is presented that identifies immobilization supports which impart additional enzyme stability. This technique models the water affinity of surface atoms with Gaussian curves, providing an enhanced mapping of hydrophobic patches (HPs), their hydrophobic intensity and their chemical nature (i.e., aromatic or aliphatic content). We explored the implications of the varied molecular surfaces of four different lipases on the preferential stabilization on random poly(sulfobetaine-co-ethylene glycol) brushes at different monomer ratios (SBMA/OEGMA), which span a wide range of hydrophobicity at the nanoscale. Activity measurements at different temperatures were performed, which revealed that some lipases of overall higher surface hydrophilicity exhibit better stability and optimal catalytic activity on more hydrophilic environments (such as *Bacillus Subtilis* Lipase A or *Rhizomucor Miehei* Lipase on SBMA-rich brushes), whereas others prefer more balanced SBMA/ OEGMA mixtures (like *Candida Rugosa* Lipase) or pure OEGMA environments which are more hydrophobic (such as *Candida Antarctica* Lipase B). Notably, the results obtained from this computational tool are able to explain that protein surface hydrophilicity and hydrophobicity play a major role in the preferential stabilization on copolymer brush surfaces of matching nature. These results can be utilized to rationally design biomaterial interfaces for boosting the stability of industrially relevant enzymes with stability issues in diverse fields, including sustainability, energy, food processing, and chemical and biological weapons defense.

In a first aspect the present invention provides a method of preparing an immobilized enzyme. The method of the first aspect can include the steps of providing a monomer-containing polymerization precursor mixture, wherein the monomer mixture comprises a hydrophilic monomer and a hydrophobic monomer in a molar ratio between 100:1 and 1:100 of hydrophilic monomer:hydrophobic monomer, performing a polymerization reaction with the precursor mixture in the presence of a substrate surface to yield a polymerized substrate comprising a copolymer brush, and contacting the polymerized substrate with an enzyme under conditions effective to allow for attachment of the enzyme to a polymer brush of the polymerized substrate. The copolymer brush can be a statistical or a random copolymer. In an advantageous embodiment the copolymer is a statistical copolymer. In further advantageous embodiments the molar ratio of hydrophilic monomer:hydrophobic monomer is selected based upon the protein surface hydrophilicity. A greater protein surface hydophilicity implicates a higher ratio of hydrophilic monomer to hydrophobic monomer in the copolymer (e.g., random copolymer).

The hydrophilic monomer or monomers can be a cationic monomer, including but not limited to [3-(methacryloylamino)propyl]trimethylammonium chloride, [2-(methacryloyloxy)ethyl]trimethylammonium chloride, and corresponding acrylates and acrylamides; an anionic monomer, including but not limited to 3-sulfopropyl methacrylate, [2-(methacryloyloxy)ethyl]dimethyl-(3-sulfopropyl)ammonium hydroxide, methacrylic acid, and corresponding acrylates and acrylamides; and other zwitterionic monomers, including but not limited to 2-methacryloyloxyethyl phosphorylcholine, and corresponding acrylates and acrylamides.

The hydrophobic monomer or monomers can be a monomer selected from the group consisting of poly(ethylene glycol) methacrylate of different molecular weights, benzyl methacrylate, cyclohexyl methacrylate, 2-(diethylamino) ethyl methacrylate, 2-(diisopropylamino)ethyl methacrylate, n-isopropylacrylamide, 2-N-Morpholinoethyl methacrylate, and corresponding acrylates and acrylamides.

In certain embodiments the method can employ a reactive monomer. The reactive monomer can be a monomer selected from the group consisting of glycidyl methacrylate and corresponding acrylates and acrylamides, as well as metal coordinating groups, such as nitrilotriacetic acid and iminodiacetic acid functionalized monomers.

In an advantageous embodiment of the first aspect, the precursor mixture includes an amine reactive cross-linking agent. The amine reactive cross-linking agent can be NHS (e.g. 1% methacrylic acid N-hydroxysuccinimide ester (NHS-MA)).

The copolymer brush can be synthesized using a "grafted from" approach or a "grafted to" approach.

The molar ratio of hydrophilic monomer:hydrophobic monomer can be a ratio selected from the group consisting of about 20:1, about 15:1, about 12:1, about 10:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:10, about 1:12, about 1:15, and about 1:20.

In an advantageous embodiment the substrate is a microsphere. In further advantageous embodiments the substrate is a microsphere. In a particularly advantageous embodiment the substrate is a silica microsphere.

The enzyme can be an enzyme group selected from the group consisting of lipase, transaminases, nitrilases, imine reductases, aldolases, ligases, N-acyltransferases, ketoreductases, hydrolases, hydrogenases, dehydrogenases, monooxygenases, peroxygenases, oxidases, halogenases, and methyltransferases. In an advantageous embodiment the enzyme is a lipase. The lipase can be a lipase selected from the group consisting of Candida rugosa lipase (CRL), Candida antarctica lipase B (CALB), Rhizomucor miehei lipase (RML), Bacillus subtilis lipase A (LipA), *Pseudomonas stutzeri* triacylglycerol lipase (lipase TL), and lipase from *Sphingomonas* sp. (HXN-200).

In a second aspect the present invention provides a second method of preparing an immobilized enzyme. The method includes the steps of providing a monomer-containing polymerization precursor mixture, wherein the monomer mixture comprises sulfobetaine methacrylate (SBMA) and poly(ethylene glycol) methacrylate (PEGMA) in a molar ratio between 100:1 and 1:100 of SBMA:PEGMA; performing a polymerization reaction with the precursor mixture to yield a copolymer brush; contacting a substrate surface with the copolymer brush under conditions effective to attach the statistical copolymer brush to the surface to yield a polymerized substrate; and contacting the polymerized substrate with an enzyme under conditions effective to allow for attachment of the enzyme to a polymer brush of the polymerized substrate.

The copolymer brush can be a statistical or a random copolymer. In an advantageous embodiment the copolymer is a statistical copolymer. In further advantageous embodiments of the second aspect the molar ratio of hydrophilic monomer:hydrophobic monomer is selected based upon the protein surface hydrophilicity. A greater protein surface hydophilicity implicates a higher ratio of hydrophilic monomer to hydrophobic monomer in the copolymer (e.g., random copolymer).

The molar ratio of hydrophilic monomer:hydrophobic monomer can be a ratio selected from the group consisting of about 20:1, about 15:1, about 12:1, about 10:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:10, about 1:12, about 1:15, and about 1:20.

In an advantageous embodiment the substrate is a microsphere. In further advantageous embodiments the substrate is a microsphere. In a particularly advantageous embodiment the substrate is a silica microsphere.

The enzyme can be an enzyme group selected from the group consisting of lipase, transaminases, nitrilases, imine reductases, aldolases, ligases, N-acyltransferases, ketoreductases, hydrolases, hydrogenases, dehydrogenases, monooxygenases, peroxygenases, oxidases, halogenases, and methyltransferases. In an advantageous embodiment the enzyme is a lipase. The lipase can be a lipase selected from the group consisting of Candida rugosa lipase (CRL), Candida antarctica lipase B (CALB), Rhizomucor miehei lipase (RML), Bacillus subtilis lipase A (LipA), *Pseudomonas stutzeri* triacylglycerol lipase (lipase TL), and lipase from *Sphingomonas* sp. (HXN-200).

In a third aspect the present invention provides a third method of preparing an immobilized enzyme. The method can include synthesizing a random statistical copolymer brush a substrate surface using a "grafted to" approach followed by contacting the polymerized substrate with an enzyme under conditions effective to allow for attachment of the enzyme to a polymer brush of the polymerized substrate.

In a fourth aspect the present invention provides an immobilized enzyme system comprising a statistical copolymer composed of a hydrophilic monomer and a hydrophobic monomer in a molar ratio between 100:1 and 1:100 of hydrophilic monomer:hydrophobic monomer forming a polymer brush affixed to a substrate surface, and further comprising an enzyme affixed to a polymer brush of the polymerized substrate. The enzyme can be from an enzyme group selected from the group consisting of lipases, transaminases, nitrilases, imine reductases, aldolases, ligases, N-acyltransferases, ketoreductases, hydrolases, hydrogenases, dehydrogenases, monooxygenases, peroxygenases, oxidases, halogenases, and methyltransferases. In an advantageous embodiment the enzyme is a lipase.

The copolymer brush of the fourth aspect can be a statistical or a random copolymer. In an advantageous embodiment the copolymer is a statistical copolymer. In further advantageous embodiments the molar ratio of hydrophilic monomer:hydrophobic monomer is selected based upon the protein surface hydrophilicity. A greater protein surface hydophilicity implicates a higher ratio of hydrophilic monomer to hydrophobic monomer in the copolymer (e.g., random copolymer).

The hydrophilic monomer or monomers can be a cationic monomer, including but not limited to [3-(methacryloylamino)propyl]trimethylammonium chloride, [2-(methacryloyloxy)ethyl]trimethylammonium chloride, and corresponding acrylates and acrylamides; an anionic monomer, including but not limited to 3-sulfopropyl methacrylate, [2-(methacryloyloxy)ethyl]dimethyl-(3-sulfopropyl)ammonium hydroxide, methacrylic acid, and corresponding acrylates and acrylamides; and other zwitterionic monomers, including but not limited to 2-methacryloyloxyethyl phosphorylcholine, and corresponding acrylates and acrylamides.

The hydrophobic monomer or monomers can be a monomer selected from the group consisting of poly(ethylene glycol) methacrylate of different molecular weights, benzyl methacrylate, cyclohexyl methacrylate, 2-(diethylamino) ethyl methacrylate, 2-(diisopropylamino)ethyl methacrylate, n-isopropylacrylamide, 2-N-Morpholinoethyl methacrylate, and corresponding acrylates and acrylamides.

In certain embodiments the method can employ a reactive monomer. The reactive monomer can be a monomer selected from the group consisting of glycidyl methacrylate and corresponding acrylates and acrylamides, as well as metal coordinating groups, such as nitrilotriacetic acid and iminodiacetic acid functionalized monomers.

In an advantageous embodiment the substrate is a microsphere. In further advantageous embodiments the substrate is a microsphere. In a particularly advantageous embodiment the substrate is a silica microsphere.

In a fifth aspect the present invention provides a kit for an immobilized enzyme system. The kit can include a statistical copolymer composed of a hydrophilic monomer and a hydrophobic monomer in a molar ratio between 100:1 and 1:100 of hydrophilic monomer:hydrophobic monomer forming a polymer brush affixed to a substrate surface. The it can further include a buffer mixture for creating conditions effective for affixing an enzyme to the polymer brush of the polymerized substrate. The molar ratio of hydrophilic monomer:hydrophobic monomer can be selected based upon the protein surface hydrophilicity. A greater protein surface hydophilicity implicates a higher ratio of hydrophilic monomer to hydrophobic monomer in the random copolymer.

In an advantageous embodiment the substrate is a microsphere. In further advantageous embodiments the substrate is a microsphere. In a particularly advantageous embodiment the substrate is a silica microsphere.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
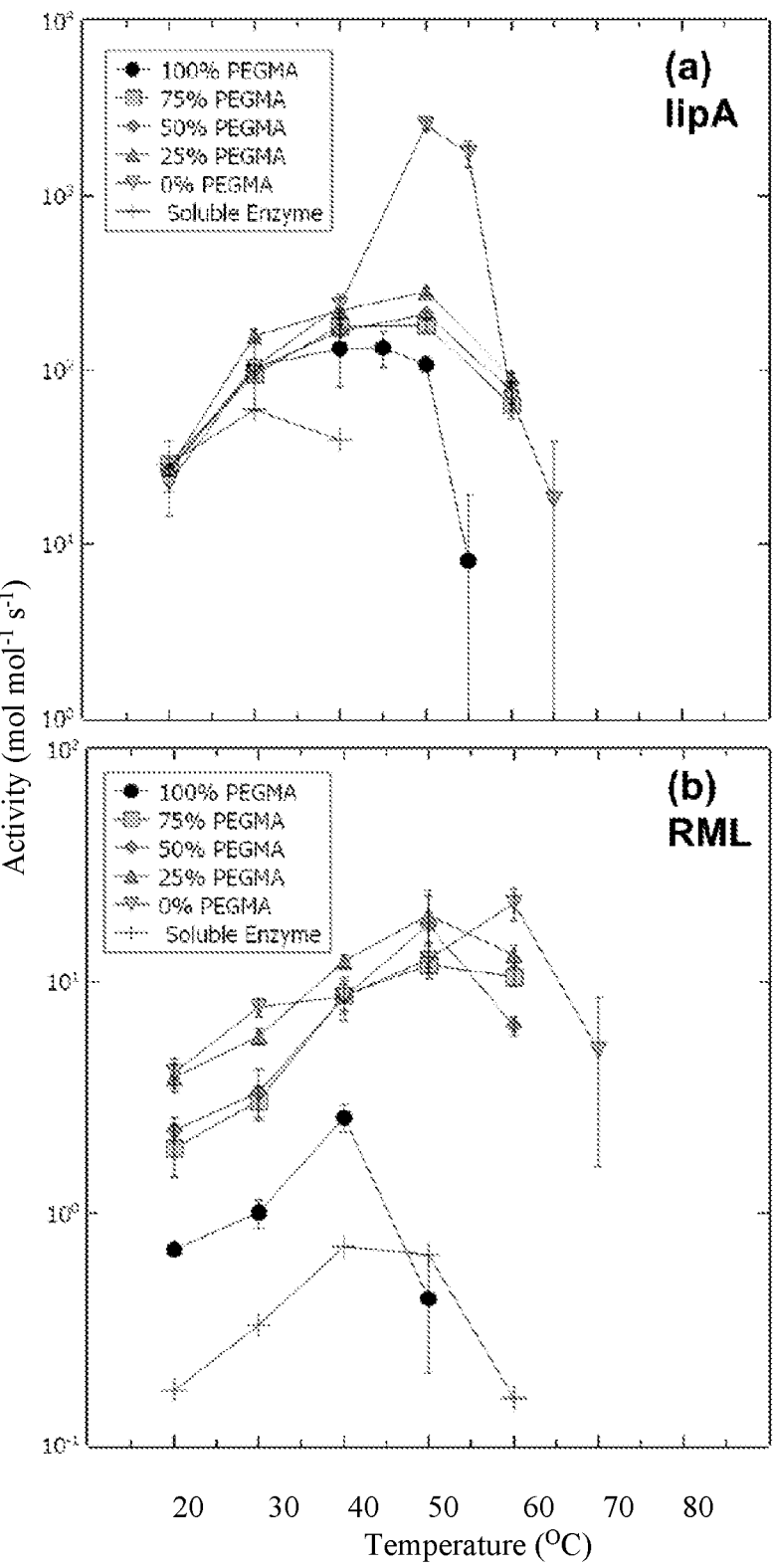
FIG. 1 is a set of four graphs ((a)-(d)) showing activity versus temperature for soluble and immobilized (a) LipA, (b) RML, (c) CRL, and (d) CALB. The composition of each brush is listed as a percent PEGMA, with the remaining composition being SBMA. Activity was measured in 50 mM sodium phosphate, pH 7.5, under moderate stirring in a temperature-controlled cuvette holder with 10 µM resorufin butyrate. The fluorescent product, resorufin, was measured and the linear rate of formation was used to calculate the rate. The background hydrolysis was subtracted for each temperature.

Polymer brushes have been created where the polymer brushes are composed of random copolymers as supports for enzyme immobilization. The composition of these heterogeneous supports can be tuned to match the heterogeneous chemical surface of an enzyme, which contained domains of varying charge and hydrophobicity. The introduction of this congruent heterogeneity of the support resulted in significant increases in immobilized enzyme stability, enabling operation of enzyme-catalyzed reactions at elevated temperatures and higher rates of catalytic turnover.

The immobilization of *Candida Rugosa* lipase to polymer brush supports composed of random copolymers of poly (ethylene glycol) methacrylate and sulfobetaine methacrylate resulted in increased stability at elevated temperatures compared to the same enzyme immobilized to neat polymer brushes composed of either monomer alone. The increased enzyme stability enabled operation of enzyme-catalyzed reactions at elevated temperatures, resulting in significant improvements in catalytic rate and catalyst operating lifetimes.

In addition, a novel machine learning-based computational technique has been developed which considers the protein surface in an all solvent exposed atom basis. By modeling the water affinity interactions by considering their variety of intensities and spatial effects with Gaussian curves, we accomplish the detection of areas of accumulated hydrophobicity, and report a detailed mapping of all the HPs, their hydrophobic intensity and their chemical nature. Further, we investigated the implications of the varied surfaces of four different lipase enzymes on the preferential stabilization by covalent immobilization on random copolymer brushes formed by sulfobetaine methacrylate (SBMA) and oligo ethylene glycol methacrylate (OEGMA) at different ratios. We performed activity measurements at different temperatures which revealed relevant insights about the interaction of the different enzymes studied with the variety of copolymer brush mixtures. Some lipases exhibit better stability and catalytic activity on more hydrophilic environments (SBMA rich brushes), whereas others prefer more balanced SBMA/OEGMA mixtures or pure OEGMA environments, which are more hydrophobic. Notably, the quantitative results obtained from the aforementioned computational tool are able to explain that protein surface hydrophilicity and hydrophobicity play a major role in the preferential stabilization on copolymer brush surfaces of matching nature. These results demonstrate that the techniques taught herein provide a means for rationally channeling the determination and syntheses of optimal engineered interfaces for enzymes of industrial relevance with long-standing stability issues in diverse fields, including sustainability, energy, food processing, and chemical and biological weapons defense.

By combining the computational study of proteins' surface hydrophobicity at the nanoscale, as well as experimental activity measurements of the four lipases BSLA, RML, CRL and CALB, we developed a comprehensive bottom-up understanding of the implications that hydrophilic and/or hydrophobic interactions have in macroscopic biocatalytic activities in biomaterial interfaces such as random copolymer brushes. By modeling the water affinity across the whole protein surface and applying a machine learning based density scanning for mapping the proteins at the nanoscale topography, HPs' morphology and hydrophobic intensity was accurately determined and reported. Further, owing to the varied chemical nature of protein residues, an aromaticity index was employed to demonstrate the rich surface heterogeneity of these lipases. We proved that hydrophobic patches with a high degree of aromaticity and scattered distribution experience less penalty to be solvent exposed than aliphatic and closely packed patches, and $\Delta G^{solv}|_{max}$ was proven to be a consistent proxy to explain the topological and chemical nature of a given HP. Further, we investigated the implications of the varied surfaces of four different lipase enzymes on the preferential stabilization by covalent immobilization on random copolymer brushes formed by different mixtures of SBMA and OEGMA. We performed activity measurements at different temperatures which revealed a variety of preferences from enzymes towards well defined copolymer brush mixtures. Some lipases exhibit better stability and catalytic activity on more hydrophilic environments (SBMA rich brushes), whereas others prefer more balanced SBMA/OEGMA mixtures or pure OEGMA environments, which are more hydrophobic. Notably, the quantitative results obtained from the hi-patch computational tool are able to explain that protein surface hydrophilicity and hydrophobicity play a major role in the preferential stabilization on copolymer brush surfaces of matching nature. These results constitute a technique for rationally channeling the determination and syntheses of optimal engineered interfaces for enzymes of industrial relevance with long-standing stability issues in diverse fields, including sustainability, energy, food processing, and chemical and biological weapons defense.

Example 1—Materials and Methods (Part 1)

Copolymer brushes will optimally include a hydrophilic monomer and a hydrophobic monomer. In some of the exemplary embodiments presented herein sulfobetaine methacrylate (SBMA) was employed as a hydrophilic monomer, poly(ethylene glycol) methacrylate (PEGMA) as a hydrophobic monomer, and 1% methacrylic acid N-hydroxysuccinimide ester (NHS-MA) was employed to enable covalent enzyme immobilization to the brush via primary amines on the enzyme surface. Alternatively, hydrophilic monomers could include cationic monomers, including but not limited to [3-(methacryloylamino)propyl]trimethylammonium chloride, [2-(methacryloyloxy)ethyl]trimethylammonium chloride, and corresponding acrylates and acrylamides; anionic monomers, including but not limited to 3-sulfopropyl methacrylate, [2-(methacryloyloxy)ethyl]dimethyl-(3-sulfopropyl)ammonium hydroxide, methacrylic acid, and corresponding acrylates and acrylamides; and other zwitterionic monomers, including but not limited to 2-methacryloyloxyethyl phosphorylcholine, and corresponding acrylates and acrylamides. Hydrophobic monomers could include other poly(ethylene glycol) methacrylate of different molecular weights, benzyl methacrylate, cyclohexyl methacrylate, 2-(diethylamino)ethyl methacrylate, 2-(diisopropylamino)ethyl methacrylate, n-isopropylacrylamide, 2-N-Morpholinoethyl methacrylate, and corresponding acrylates and acrylamides. For enzyme immobilization, other reactive monomers, including but not limited to, glycidyl methacrylate and corresponding acrylates and acrylamides could be employed, as well as metal coordinating groups, such as nitrilotriacetic acid and iminodiacetic acid functionalized monomers.

Materials: *Candida rugosa* lipase (CRL), *Candida antarctica* lipase B (CALB), and *Rhizomucor miehei* lipase (RML) where purchased from Sigma Aldrich and used without further purification. *Bacillus subtilis* lipase A (LipA) was expressed and purified as previously described. Polydisperse silica microspheres (1-3 μm) were purchased from Nanocym and cleaned with UV-ozone before functionalization. Resorufin butyrate (RB), copper (I) bromide, 2-2'-bipyridyl (Bpy), methacrylic acid N-hydroxysuccinimide ester (NHS-MA), and [2-(methacryloyloxy)ethyl]dimethyl-(3-sulfopropyl)-ammonium hydroxide (SBMA) were purchased from Sigma-Aldrich and used as received. Poly(ethylene glycol) methacrylate ($M_n$=360 Da, PEGMA) was purchased from Sigma Aldrich and passed over basic alumina before polymerization. (p-chloromethyl)phenyltrichlorosilane (CMPS) was purchased from Gelest and used as received.

Surface Functionalization: Polydisperse microspheres (2.5 g) were cleaned with UV-Ozone for one hour before silanization with CMPS. Cleaned microspheres were added to 30 mL of toluene with moderate stirring, to which 0.3 mL CMPS was added. Silanization was left for 45 minutes at room temperature before being filtered and serially rinsed with toluene, methanol, and distilled water. Functionalized particles were dried and stored in a vacuum desiccator prior to siATRP.

siATRP: Homopolymer and statistical copolymer brushes synthesized using a "grafted from" approach from initiator functionalized silica microspheres using atom transfer radical polymerization (ATRP), as previously described. Briefly, polymerization reactions were prepared in trifluoroethanol (TFE) with a molar ratio of 100-x:x:1:5:2:0.2 of SBMA, PEGMA, NHS-MA, bpy, Cu(I)Br, Cu(II)Br, respectively, where x is the amount of PEGMA in the feed as a percentage. Additionally, 1 mole percent of NHS-MA was added to the feed for covalent attachment of the enzymes via primary amines on the enzyme surface. All reactants were added to the polymerization reaction except the functionalized silica microspheres, and the reaction was degassed with three freeze pump thaw cycles. On the final freeze cycle, the silica microspheres were added to the Schlenk flask. Polymerization was left at room temperature for 24 hours, and polymerization reactions were terminated by exposing the reaction to air. Polymerized microspheres were filtered and thoroughly rinsed with warm TFE before being dried and stored in a vacuum desiccator before immobilization.

Enzyme Immobilization: Enzymes were immobilized by mixing 10 mg of particles with 800 μL of enzyme at 2 mg/mL in 50 mM sodium phosphate, pH 7.5. Immobilization reactions proceeded overnight at 4° C. with mild shaking to suspend microspheres. The amount of enzyme immobilized was determined by measuring the remaining activity in the supernatant and subsequent rinses of the particles with the same buffer.

Enzyme Activity Measurements: Enzyme activity of all lipases was measured with the fluorogenic substrate resorufin butyrate which forms the fluorescence product resorufin by hydrolysis of the butyric ester. Reactions were performed at 10 μM substrate concentration in sodium phosphate, pH 7.5. Reactions were monitored in a fluorometer (Fluoromax-4, Horiba) with 570 nm excitation and 593 nm emission wavelengths using continuous stirring in a temperature-controlled cuvette holder. The initial linear rate of product formation before 10% conversion was used to determine the rate at each temperature. Fluorescence intensity was associated to concentration by using a standard calibration curve for resorufin. Background hydrolysis was subtracted for each temperature. Excitation and emission wavelengths used were 570/593 nm respectively.

Example 2—Enzyme Immobilization to Heterogeneous Polymer Brushes for Improved Stability In order to evaluate the effect of immobilization chemistry on the stability of the immobilized enzyme, the temperature dependence of activity was measured for the soluble enzyme and the enzyme immobilized to polymer brushes of different compositions (FIG. 1). The temperature dependence of activity is a convenient method to determine the high temperature stability of an enzyme while simultaneously providing valuable information about the performance of the catalyst. Typically, enzyme-catalyzed reactions will increase exponentially with increasing temperature, in accordance with Arrhenius equation, until increased temperatures cause enzyme inactivation. High temperature inactivation is due to denaturation (i.e., loss of folded enzyme structure) or aggregation, with the latter not possible for immobilized enzymes. Therefore, an increase in the temperature optimum of activity indicates increased high temperature stability of the enzyme.

In the case of lipase A from *Bacillus subtilis* (lipA), the temperature optimum of activity of immobilized lipA was greater for both homopolymers and statistical copolymers support compositions compared to the soluble enzyme, indicating stabilization upon immobilization in all cases (FIG. 1a). The temperature optimum of activity was 50° C. for lipA immobilized to 0%, 25%, 50%, and 75% PEGMA brushes (100%, 75%, 50%, and 25% PEGMA, respectively) indicating greater high temperature stability on these support compositions than on homopolymer PEGMA brushes. This indicates chemical heterogeneity increased the high temperature stability compared to hydrophobic homopolymers for lipA.

For *Rhizomucor miehei* lipase (RML), the temperature optimum of activity was greater for 0%, 25%, 50%, and 75% PEGMA than either 100% PEGMA or the soluble enzyme (FIG. 1B). Notably, this enzyme was less stable on the 100% PEGMA support than in solution, suggesting a homopolymer of this composition was destabilizing. Conversely, all statistical copolymers appeared stabilizing relative to the soluble enzyme or immobilized on the 100% PEGMA homopolymer support.

In the case of *Candida rugosa* lipase (CRL), the temperature optimum of activity was greatest for the mixtures (i.e., 25%, 50%, and 75% PEGMA) than for either homopolymer, indicating that statistical copolymers were the most stabilizing of any conditions tested (FIG. 1c).

For *Candida antarctica* lipase B (CALB), the greatest temperature optimum of activity was observed on the for 100% PEGMA (FIG. 1d). However, the 75% PEGMA had a greater temperature optimum than the other statistical copolymers or homopolymer SBMA (0% PEGMA), indicating the statistical copolymers provided greater stabilization compared to the hydrophilic SBMA homopolymer support.

The composition that resulted in the greatest stabilization was different for each enzyme, and in the case of RML, the most stabilizing composition of the immobilization support were statistical copolymers composed of hydrophilic and hydrophobic monomers. This provides an important design criterion for enzyme immobilization where increased stability is desired.

Due to the Arrhenius relationship between temperature and rate, a modest increase in high temperature stability leads to exponentially higher rates of reaction at higher temperatures. This is especially important for industrial catalysis, where less enzyme is needed to achieve the same conversion, and for biosensing, where higher rates increase the sensitivity. Additionally, it has been demonstrated that improved high temperature stability of immobilized enzymes corresponds to greater solvent tolerance. [Iyer, P. V.; Ananthanarayan, L. Enzyme Stability and Stabilization-Aqueous and Non-Aqueous Environment. *Process Biochem.* 2008, 43 (10), 1019-1032.] This is important in industrial catalysis, where desired substrates or products are insoluble in water, or where water plays a role in the catalytic mechanism and a reduction in water concentration can change the direction of the reaction. This is especially important for lipases, where non-aqueous catalysis can be used to synthesize esters, whereas in water ester hydrolysis is favored.

Herein, we demonstrate that four diverse, industrially important lipases achieved greater high-temperature stability when immobilized to statistical copolymers composed of hydrophilic and hydrophobic monomers compared to homopolymer brushes. Given the diversity of the physical properties of the lipases investigated herein, it is likely this result universally applies to all enzymes. While the mechanism of stabilization is a matter of speculation, it is possible that heterogeneous polymers match the chemical heterogeneity of the surface of the enzyme. The surfaces of enzymes, while generally hydrophilic, contain discrete, connected regions of hydrophobic moieties, which vary in size and frequency. [Jacak, R.; Leaver-Fay, A.; Kuhlman, B. Computational Protein Design with Explicit Consideration of Surface Hydrophobic Patches. *Proteins Struct. Fund. Bioinforma.* 2012, 80 (3), 825-838.] Congruence between polymer support and the enzyme surface leads to many favorable stabilizing interactions. Therefore, in the context of this work, the term hydrophobic could include any moiety which makes favorable interactions with hydrophobic patches on the enzyme surface. This may include monomers that are traditionally not referred to as hydrophobic due to water solubility or wettability.

Example 3—Materials and Methods (Part 2)

Materials: *Bacillus Subtilis* Lipase A (BSLA), *Candida Rugosa* Lipase (CRL), *Candida Antarctica* Lipase B (CALB) and *Rhizomucor Miehei* Lipase (RML) were purchased from Sigma Aldrich. Polydisperse silica microspheres (1-3 μm) were purchased from Nanocym. Resorufin butyrate (RB), copper (I) bromide, 2-2'-bipyridyl (Bpy), methacrylic acid N-hydroxysuccinimide ester (NHS-MA), oligo ethylene glycol methacrylic acid ester ($M_n$=300 Da, OEGMA) and [2-methacryloyloxy)ethyl]dimethyl-(3-sulfopropyl)-ammonium hydroxide (SBMA) were purchased from Sigma-Aldrich. (p-chloromethyl)phenyltrichlorosilane (CMPS) was purchased from Gelest. All non-protein compounds were used without further purification.

Surface preparation and polymer functionalization: 1-3 μm diameter polydisperse microspheres (2.5 g) were suspended in 30 mL of toluene with moderate stirring in a PTFE beaker and 1 mL of CMPS. Particles were filtered in vacuo, washed with toluene and 2-propanol, and stored in a desiccator before next steps.

Random copolymer brushes were grown with an ATRP living polymerization from the surface of the microspheres using the CMPS monolayer as initiator. Microspheres and monomer-containing polymerization precursor mixtures of OEGMA and SBMA ranging concentrations spanning 0% to 100% molar ratio—where percentages refer to OEGMA content, and the complementary refers to SBMA content—, namely 0, 25, 50, 75 and 100%, were prepared in 5 mL 2,2,2-Trifluoroethanol (TFE). Precursor solutions contained 1.29 g of SBMA for 0% OEGMA, and 1.20 g of OEGMA for 100% OEGMA. To promote covalent binding, 0.0073 g of NHS-MA were also added (1% in molar ratio). A second solution containing 0.022 g of CuBr and 0.0624 g of Bpy was made in 10 mL TFE and continuously stirred until CuBr fully dissolved. Both solutions were degassed in Schlenk flasks through three freeze-thaw cycles under vacuum to remove dissolved $O_2$, then, the copper-containing solution was transferred to the flask containing the microspheres and monomer mixture under a $N_2$ inert atmosphere and left reacting for 24 h at a positive pressure of 5 psi. Polymer-brush coated microspheres were retrieved through vacuum filtration and sequentially washed in three cycles with TFE and anhydrous 2-propanol; and stored in a desiccator until further use.

Protein immobilization: All enzymes were dialyzed previous to immobilization reactions. BSLA, CRL, CALB and RML were dialyzed against an 8 M urea solution and refolded by diluting 1:20 into 50 mM phosphate buffer at pH 7.5 prior to immobilization. Immobilization reactions were carried out by mixing 1 mg of polymer brush-coated microspheres with 800 μL of $10^{-5}$ M protein and rotating in a tube revolver at 4° C. for 12 h.

Loading on the microspheres was calculated through a mass balance by making several washes, supernatant retrievals and measuring their concentration though activity measurements.

Activity assays: Precalculated enzyme loading on microspheres was utilized in order to normalize the concentration of enzymes in each reaction vessel. Enzyme activities were determined from the slope of the initial rate of product formation at the $V_{max}$ region through continuous fluorescence intensity tracking. Fluorescence intensity was associated to concentration by using a standard calibration curve for resorufin at the same conditions of reaction measurements. All substrate hydrolyses at different conditions (i.e. temperatures) were subtracted from activity measurements to rule out non-catalytic background hydrolysis. Excitation and emission wavelengths used were 570/593 nm respectively.

Thermal stability profiles were measured in a Fluoromax-4 (Horiba) fluorimeter at a final volume of 3 mL and mild stirring. Buffer solutions were preheated to the target temperatures in an external water bath and cuvettes were loaded in an embedded Peltier system attached to the fluorimeter to maintain the temperature. Substrates and enzymes (soluble or immobilized) were added in aliquots of negligible volume to prevent major temperature shifts.

All activity assays were carried out in 50 mM pH 7.5 phosphate buffer.

Figure 2:
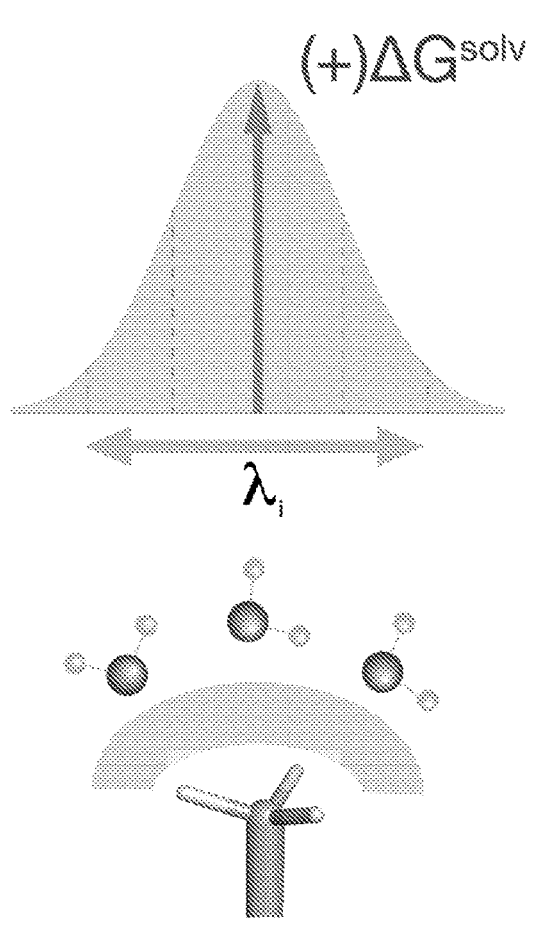
FIG. 2 is an illustration providing a representation of Gaussian modeling of hydrophobic interactions (left, positive $\Delta G^{solv}$) and hydrophilic interactions (right, negative $\Delta G^{solv}$) in the surface of a protein.
Figure 2:
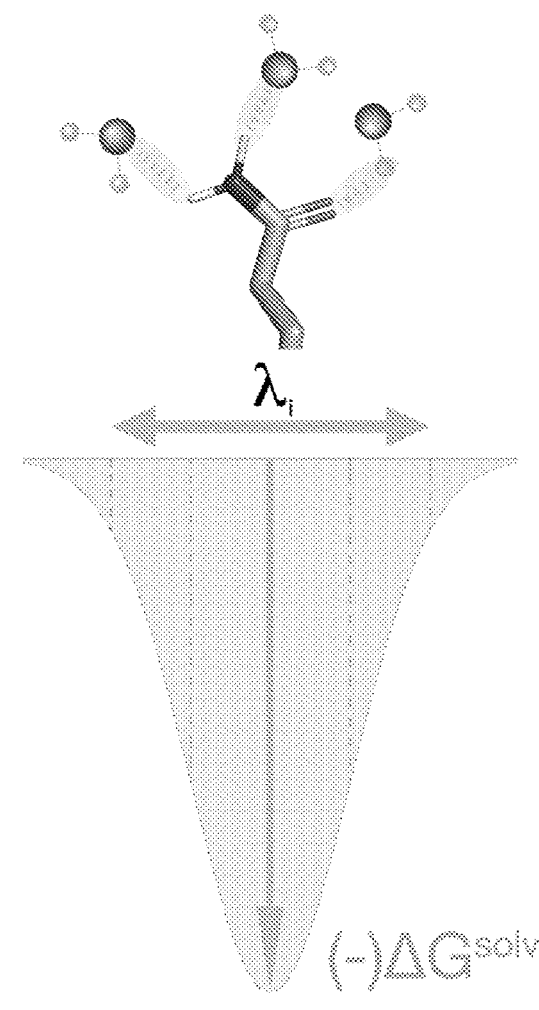

Computational analysis: Crystal structures obtained from the Protein Data Bank were utilized to study all protein structures. PDB files used for different proteins were 1ISP (LipA), 1GZ7 (CRL), 4K6G (CalB) and 3TGL (RML). Metadata from the PDB files and non main polypeptide information were cleaned (i.e. leaving a single polypeptide chain, removing all water molecules, hydrogens, substrates and cofactor molecules) and exported to an Excel spreadsheet. Once cleaned, PDB files are opened in Pymol 2.4 and an in-house Python script is used to calculate the solvent accessible surface area of each specific atom, and these values are also exported to the spreadsheet. A MatLab script was developed and utilized to study the surface properties of the proteins (FIG. 2). For each atom i in the crystal structure, the solvent accessible surface area (i.e., the Van der Waals radius plus water radius) of a single atom is calculated, and the fractional solvent accessible surface area ($\gamma_i$) is defined as:

$$\gamma_i = \frac{SASA_{cs,i}}{SASA_{sphere,i}}$$

where $SASA_{cs,i}$ is the calculated solvent accessible surface area for an atom i in the crystal structure, and $SASA_{tot,i}$ is the total solvent accessible surface area of a spherical free-form isolated atom i. All atoms with $\gamma_i < 2\%$ (fully buried or negligibly solvent exposed) are filtered out (FIG. 3a) and disregarded during the surface analysis.

The variety of effects related to the hydrophilicity/hydrophobicity of protein surface atoms with water (i.e., propensity/inability of hydrogen bonding, ion hydration, Van der Waals forces) are accounted for by utilizing the free energies of solvation ($\Delta G^{solv}$) of each individual atom depending on their nature within the polypeptide. The free energy of solvation of an atom i in the crystal structure without neighboring effects ($\Delta G^{solv}|_{cs,i}$) is calculated as follows:

$$\Delta G^{solv}|_{cs,i} = \Delta G^{solv}|_{free,i} \cdot \gamma_i$$

where $$\left(\Delta G^{solv}|_{free,i}\right)$$

is the theoretical free energy of solvation of a free-form spherical atom i.

In order to map hydrophobic patches (HPs) in the surface of the proteins, i.e., atoms in spatial proximity and significant hydrophobic intensity; a modified form of the previously used "motion blur Point Accumulation for Imaging in Nanoscale Topography" (mbPAINT) technique is used. The strength of the hydrophobic interaction with the solvent of each atom (quantified by means of solvation free energies, $$\Delta G^{solv}),^{44,45}$$

as well as the effect on the surrounding atoms, is modeled as a Gaussian curve (FIG. 1) whose amplitude corresponds to $$\Delta G^{solv}|_{cs,i},$$

and standard deviation corresponds to a solvation characteristic length ($\lambda_i$) of 3.5 Å for uncharged atoms and 6 Å for charged atoms,[45] multiplied by a correction factor (¼). The cumulative hydrophobic intensity of each atom corresponds to the amplitude of the own atom's Gaussian ($\Delta G^{solv}|_{cs,j}$), and the contribution from the Gaussian tails from the surrounding atoms i at the corresponding inter atomic distance, according to the expression:

$$\Delta G^{solv}|_{cs,i}$$

where $$\Delta G^{solv}|_{cum,j}$$

is the cumulative free energy of solvation of an atom j in the surface, $$\Delta G^{solv}|_{cum,j} = \sum_{i}^{n} \Delta G^{solv}|_{cs,i} \cdot \exp\left(-\frac{8 \cdot d_{ji}^2}{\lambda_i^2}\right)$$

is the isolated free energy of solvation of a neighboring atom i, n is the total number of solvent accessible atoms in the crystal structure and $d_{ji}$ is the distance between atom j and a neighbor i.

Figure 3:
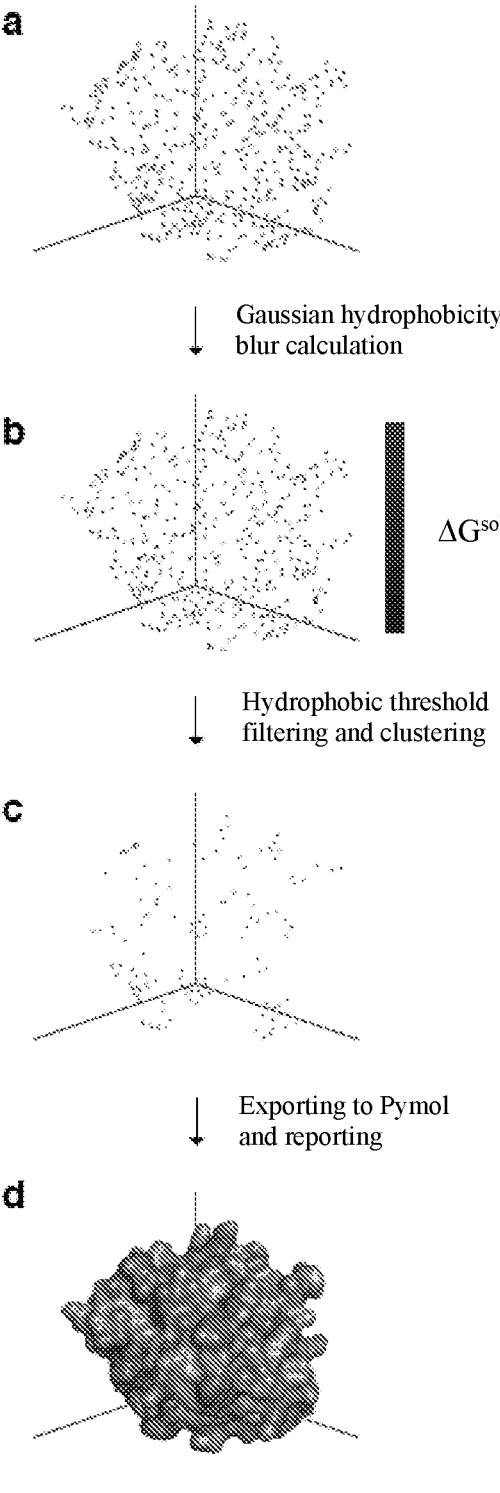
FIG. 3 is a set of five illustrations (a-e). (a) Spatial arrangement of solvent exposed atoms in the crystal structure after solvent exposure filtering. (b) Representation of accumulated solvation free energy of each atom. (c) Spatial arrangement of surface atoms that are hydrophobic and belonging to a HP. (d) Pymol representation of HPs (red—not visible in gray scale) on the surface of a protein. (e) Pymol representation of HPs (dark gray) on the surface of a protein.

Once $\Delta G^{solv}|_{cum,j}$ are calculated (FIG. 3b), atoms in a hydrophobic environment $$\left(\Delta G^{solv}|_{cum,j} > 0\right)$$

are considered for HP clustering analysis. A machine learning clustering technique, termed "Density-Based Spatial Clustering of Applications with Noise" (DBSCAN), available as a function in the machine learning and statistical package of MatLab, is used to cluster atoms as part of a same HP or different. The minimum number of spatially close atoms to consider a patch was set to 4, and the neighbor search radius (ε, i.e., radius within which other data points need to be to be considered part of the same cluster) was set to three times the radius of water (1.4 Å). All atoms considered as noise, even though hydrophobic, are considered not to be part of HPs for the analysis (FIG. 3c). Further, atoms in the protein structure are ranked based on their aliphatic/aromatic nature, a binary assignment is made (0=aliphatic, 1=aromatic) and an aromaticity index is defined to classify the chemical nature of each HP. Every patch stores the information of spatial arrangement of each belonging atom and their $$\Delta G^{solv}|_{cum},$$

surface area and aromaticity index. The atoms belonging to each hydrophobic patch are output in Pymol format in order to be exported and visualized (FIG. 3d). The free energy of solvation of the whole protein $$\left(\Delta G^{solv}|_{prot}\right)$$

is calculated as:

$$\Delta G^{solv}|_{prot} = \sum_{j}^{n} \Delta G^{solv}|_{acc,j}$$

Calculation of Activity Weighted Copolymer Composition.

Figure 9:
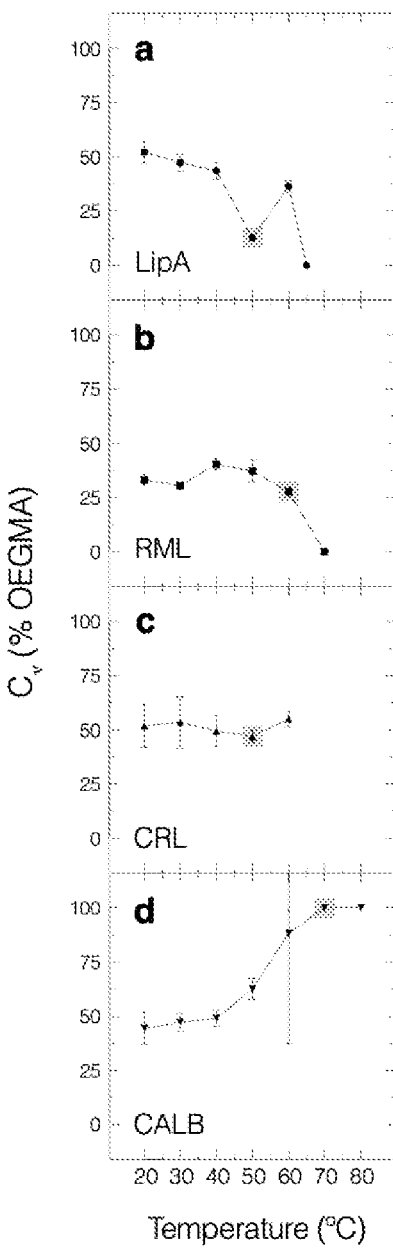
FIG. 9 is a set of four graphs ((a)-(d)) of activity weighted composition profiles. (a) Activity weighted composition profile of BSLA at different temperatures. (b) Activity weighted composition profile of RML at different temperatures. (c) Activity weighted composition profile of CRL at different temperatures. (d) Activity weighted composition profile of CALB at different temperatures. Highlighted are the data points corresponding to the maximum activity of each lipase, which corresponds to the optimal temperature $T_{opt}$. The error bars represent the standard error of the mean for three replicated measurements (n=3).

In order to calculate the copolymer brush compositions at which the enzymes show preferential stability at different temperatures, an "activity weighted composition" ($\overline{C}_v$) was defined as:

$$\overline{C}_u = \sum_{i}^{n} \left( C_i \cdot \frac{v(C_i)}{\sum v(C_i)} \right)$$

$$\gamma_i = \frac{SASA_{cs,i}}{SASA_{sphere,i}}$$

where $C_i$ is a copolymer brush composition, expressed in terms of % OEGMA, n is the number of different copolymer compositions studied, and $v(C_i)$ is the specific activity of each lipase immobilized on a given copolymer brush. The values of $\overline{C}_v$ were calculated at each temperature for the different lipases in order to construct the activity weighted composition profiles shown in FIG. 9.

Example 4—Computational Analysis of Protein Surface Hydrophobicity

In order to investigate the implications of the heterogeneity of lipase surfaces in their interaction with polymer brush interfaces of different nature based on the hydrophobic interactions, a script was devised to characterize the topology and intensity of the hydrophobicity in the surface of lipases. *Bacillus Subtilis* Lipase A (LipA), *Candida Rugosa* Lipase (CRL), *Candida Antarctica* Lipase B (CalB) and *Rhizomucor* Michel Lipase (RML) (PDB ID's: 1ISP, 1GZ7, 4K6G, 3TGL, respectively) were considered for the analyses.

Crystal structures obtained from the Protein Data Bank were considered in an atom basis. The information contained in the PDB files (spatial coordinates of atoms and primary sequence order) was prepared and exported to Excel spreadsheets as a single polypeptide, whereas other elements such as other polypeptide chains, water molecules, cofactors, substrates, ions and hydrogen atoms were disregarded for the analyses. Moreover, the solvent accessibility of each atom within the crystal structure was calculated with an in-house script.

The affinity of each atom with water was quantified by means of the free energy of solvation ($\Delta G^{solv}$) of each atom and was modeled as a Gaussian curve, where the amplitude corresponds to the $\Delta G^{solv}$ of the given atom, negative for hydrophilic interactions and positive for hydrophobic interactions; and the standard deviation corresponds to a characteristic length scale ($\lambda_i$) (FIG. 2). The variety of effects related to the hydrophilicity/hydrophobicity of protein surface atoms with water (i.e., propensity/inability of hydrogen bonding, ion hydration, Van der Waals forces) are accounted for in the value of $\Delta G^{solv}$. The distance dependence of the Gaussian curves served as a tool to investigate the influence of hydrophilicity or hydrophobicity on neighboring atoms. The cumulative $\Delta G^{solv}$ of an atom on the folded protein surface corresponds to the amplitude of its Gaussian curve, plus the contribution from the Gaussian curves belonging to all other solvent exposed atoms in the crystal structure, although only atoms in spatial proximity make a significant contribution.

Figure 7:
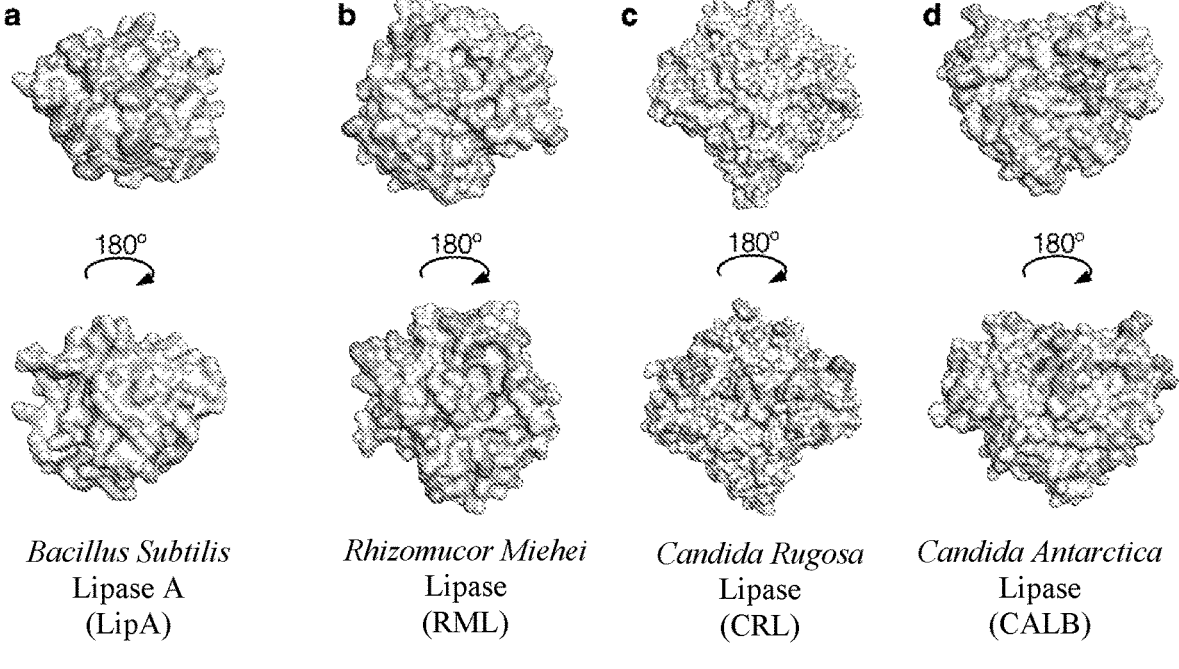
FIG. 7 is a set of four illustrations ((a)-(d)) of crystal structures. (a) Crystal structure of BSLA and hydrophobic patches determined with hi-patch. (b) Crystal structure of RML and hydrophobic patches determined with hi-patch. (c) Crystal structure of CRL and hydrophobic patches determined with hi-patch. (d) Crystal structure of CALB and hydrophobic patches determined with hi-patch.
Figure 8:
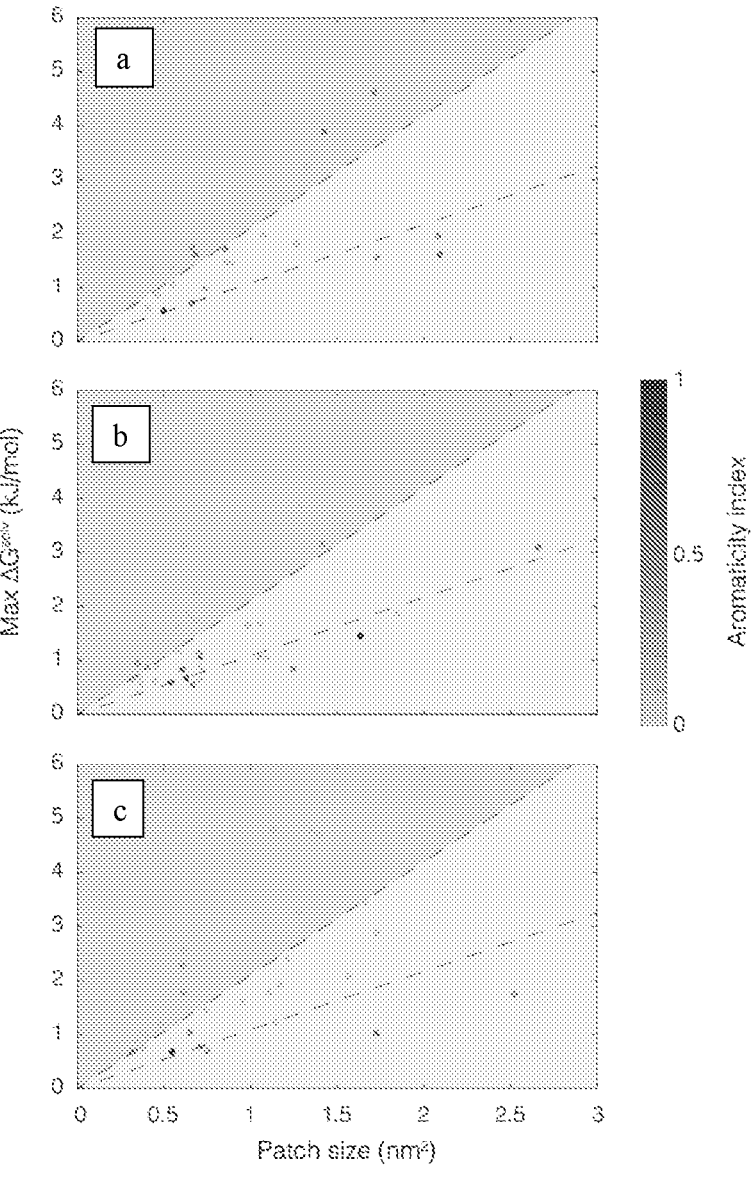
FIG. 8 is a set of three graphs ((a)-(c)) (a) Patch topology plot of RML showing three different regions based on aromaticity and spatial arrangement of the atoms belonging to a HP. (b) Patch topology plot of CRL. (c) Patch topology plot of CALB.

In order to map HPs in the surface of the proteins (i.e., atoms in spatial proximity and significant hydrophobic intensity), a modified form of the "motion blur Point Accumulation for Imaging in Nanoscale Topography" (mbPAINT) technique is used. First, the surface accessibility of each atom in the crystal structure is utilized to filter out all the buried atoms, such that only solvent accessible surface (SAS) atoms (FIG. 2a) are considered in the hydrophobicity analysis. Gaussian curves of the SAS atoms are calculated, and each atom stores the information of the cumulative $\Delta G^{solv}$ (FIG. 3b). To segregate hydrophobic atoms among the solvent accessible ones, all the atoms with $\Delta G^{solv}$ above a hydrophobicity threshold ($\Delta G^{solv}>0$) are regarded for the clustering analysis. A clustering technique termed "Density-Based Spatial Clustering of Applications with Noise" (DBSCAN), is used to group atoms as part of different HPs, and all atoms considered as noise, even though hydrophobic, are considered not to be part of HPs for the analysis (FIG. 3c). Indeed, this noise neglecting application aligns well with the fact that at the nanoscale in the protein surface, single hydrophobic atoms are not able to form dewetted gaps. Then, HP information is output in Pymol format for quick visualization of the results (FIG. 3d). The spatial arrangements of HPs in the crystal structures of the four lipases considered in this study were determined and output for observation (FIG. 7). For each determined HP, different information can be extracted or calculated: size of the patch (i.e., surface coverage, number of residues, number of atoms involved . . . ), total patch $\Delta G^{solv}$ or maximum $\Delta G^{solv}$, ($\Delta G^{solv}|_{max}$) achieved within the patch. We termed this script "hi-patch", standing for "hydrophobic intensity patch", as an upgrade of the very established "hpatch", by enhancing the output of hydrophobic patches by providing the hydrophobic intensity of those, as well as an enhanced mapping through the machine learning based density scanning.

Figure 4:
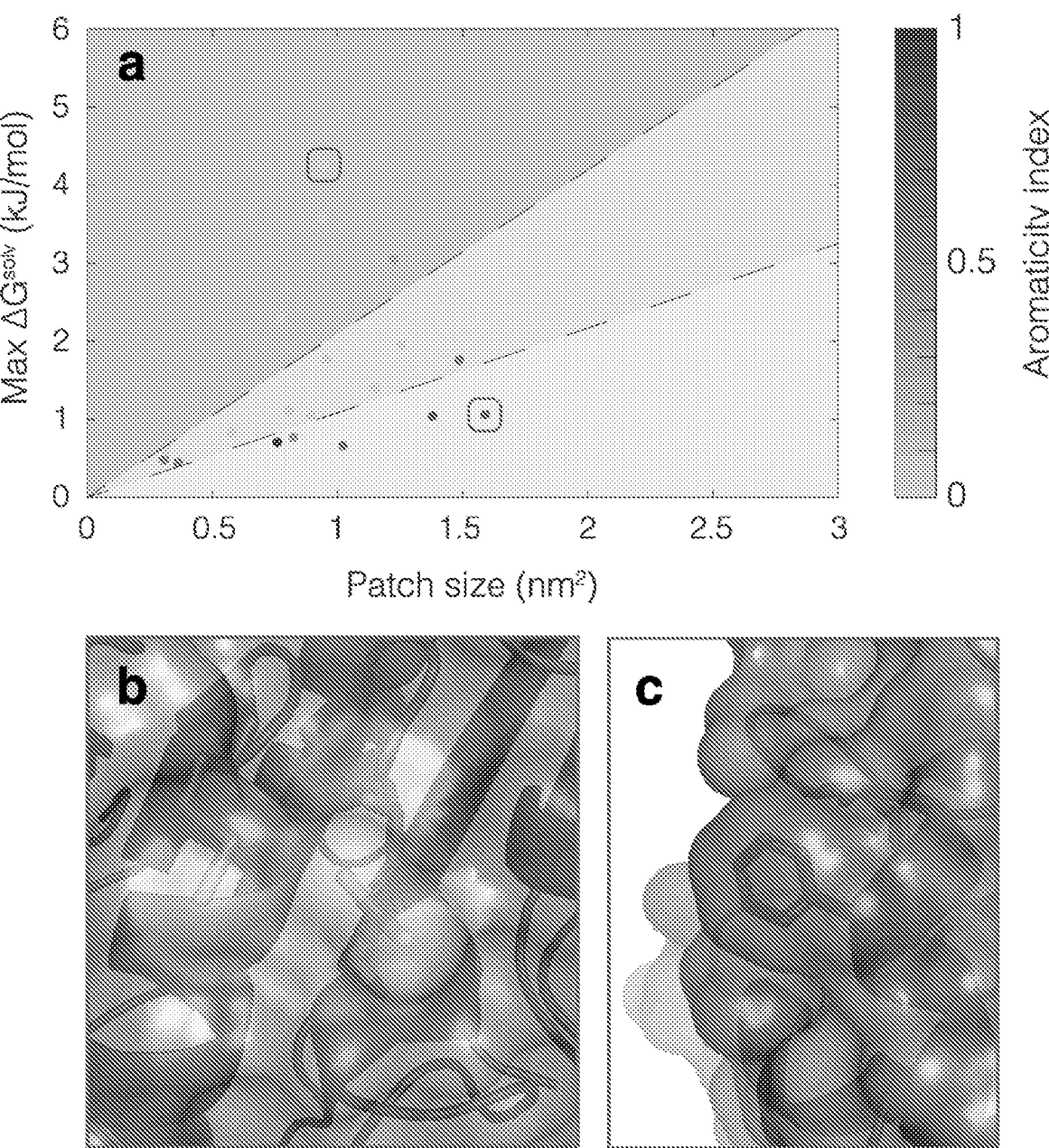
FIG. 4 is a graph (a) and two illustrations (b and c). (a) Patch topology plots of BSLA showing three different regions based on aromaticity and spatial arrangement of the atoms belonging to a HP. The low region (light gray) represents HPs of mostly aromatic nature and sparse arrangement, the intermediate region between the dashed lines represents a mixed region with HPs of intermediate aromaticity, sparsely arranged aliphatic HPs or closely packed aromatic HPs; and the upper region (dark gray) depicts HPs of closely packed aliphatic atoms. (b) Representation of the HP patch with the highest $\Delta G^{solv}|_{max}$ of BSLA. (c) Representation of the HP patch with the largest area of BSLA.

The value of $\Delta G^{solv}|_{max}$, given the nature of the distance dependent calculation, indirectly provides valuable topological information about each different patch. For instance, atoms in close spatial proximity will achieve higher values of $\Delta G^{solv}|_{max}$ than more separated ones for the same solvent exposed hydrophobic atoms. In order to investigate this effect, as well as the chemical nature of the atoms belonging to each HP, an aromaticity index was defined. This aromaticity index relies on the binary assignment to each atom based on its aliphatic or aromatic nature (aliphatic=0, aromatic=1). Therefore, once the HP assignment has been carried out by means of the DBSCAN clustering algorithm, the aromaticity index of each HP can be examined. An interesting effect of the aromaticity $\Delta G^{solv}|_{max}$ could be observed for patches of different sizes. Patches of a low degree of aromaticity (i.e., mostly aliphatic) showed remarkably higher values of the $\Delta G^{solv}|_{max}$ per unit size, whereas patches with a higher degree or aromaticity, displayed smaller values, although they showed the tendency to form larger patches. This behavior elucidates a penalty of aliphatic patches to be large in size, which aligns with the fact that the $\Delta G^{solv}$ values of aliphatic atoms are larger in magnitude (i.e., more hydrophobic) than those of aromatic atoms, and therefore, have higher propensity to be buried in hydrophobic pockets. Upon plotting the $\Delta G^{solv}|_{max}$ of each HP versus their size and observing individually the morphology of the patches, three regions of different patch natures could be determined for BSLA (FIG. 4). A first region, in dark gray above the upper dashed slope represents HPs of low aromaticity and close atom surface packing. FIG. 4b depicts a representative patch of this region, which is the patch of largest $\Delta G^{solv}|_{max}$ in BSLA. A second region, in medium gray, represents a variety of HP natures: HPs of intermediate aromaticity, HPs of low aromaticity with sparse spatial arrangement, and HPs of high aromaticity with close spatial proximity. A third region, in light gray and below the lower dashed line, corresponding to atoms of low $\Delta G^{solv}|_{max}$ values and high degree of aromaticity, which display a sparse spatial arrangement. FIG. 4c depicts a representative HP from this high aromaticity and large surface region. The same analysis was carried out for all other three crystal structures (FIG. 7), and the grayed regions determined from the BSLA crystal structure seemed to hold surprisingly well for the other lipases.

Example 5—Differential Catalytic Activity of Lipases Immobilized on Random Copolymer Brush Mixtures The aforementioned lipases displayed a varied preferential stability by being immobilized on pure [2-methacryloyloxy)ethyl]dimethyl-(3-sulfopropyl)-ammonium hydroxide (SBMA) or pure oligo ethylene glycol methacrylate (OEGMA) polymer brushes, results which suggest the heterogeneous nature of different lipases. The underlying phenomenology which would explain the preference of different lipases to different polymers, or even, to different copolymer mixtures, remains incompletely understood. To explore and develop an understanding of the implications of the surface heterogeneity of lipases on their affinity to different polymer brush environments, random copolymer brushes containing different contents of SBMA and OEGMA were synthesized on silica microspheres of 2 µm of average diameter. The brushes were synthesized with OEGMA and SBMA at ranging concentrations spanning 0% to 100% molar ratio—where percentages will refer to OEGMA content, and the complementary refers to SBMA content—, namely 0, 25, 50, 75 and 100% OEGMA, and subsequently, 100, 75, 50, 25 and 0% SBMA. Additionally, methacrylic acid N-hydroxysuccinimide ester (NHS-MA) was added at a 1% content. With the presence of NHS in the copolymer brush backbones, covalent attachment of the lipases through primary amines present on their surface was possible. Previous work demonstrated that surfaces with grafted SBMA/OEGMA copolymer brushes of a variety of compositions displayed ranging water affinity. Macroscopic hydrophilicity differences could be observed through contact angle measurements; but most importantly, a nanoscopic hydrophilicity variation and decrease of hydrophobic adsorption sites could be observed as the content of SBMA increased, which demonstrates the ability to systematically tune the nanoscale hydrophilicity of the copolymer brush surfaces, and subsequently, study how these environments interact with the varied lipase surfaces.

Figure 5:
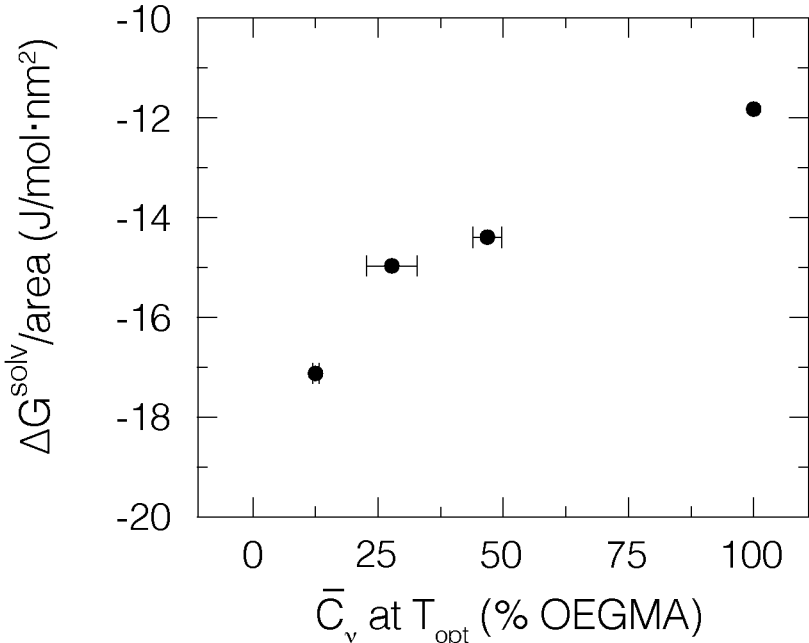
FIG. 5 is a graph showing the accumulated free energy of solvation per area of the whole protein surface (considering both patch-belonging and non-patch-belonging regions of four different lipases versus their activity weighted composition at their $T_{opt}$. The error bars represent the standard error of the mean for three replicated measurements (n=3).
Figure 6:
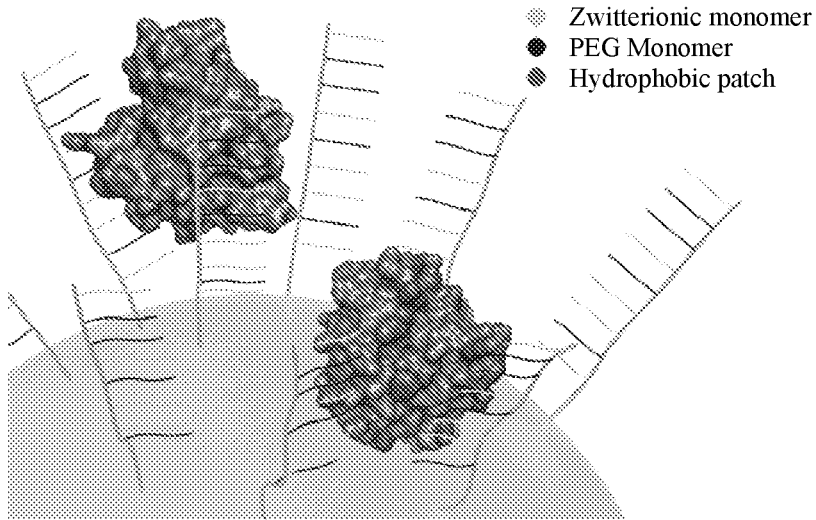
FIG. 6 is an illustration depicting an enzyme having hydrophobic patches immobilized on a copolymer brush.

The activity-stability relationship of the lipases upon their covalent immobilization on the various copolymer brush compositions was tested through temperature activity profiles (i.e., specific activity versus reaction temperature), at ranging temperatures of 20 to 80° C. (FIG. 5). Immobilization of BSLA, CRL, CALB and RML on the different copolymer brushes resulted in a variety of stability responses. BSLA and CALB displayed their stability maxima upon immobilization on pure SBMA and pure PEGMA respectively, with a gradual stability decay as the concentration of the complementary monomer increased. These profiles shed light to the difference of surface heterogeneity that leads BSLA (FIG. 1a) to be notoriously better stabilized (according to the catalytic activity at different temperatures) in more hydrophilic surfaces and lose stability as it is immobilized on brushes with more nanoscale hydrophobicity; and CALB (FIG. 1d) to be preferentially stabilized on more hydrophobic surfaces and lose stability on more hydrophilic surfaces. Notably, RML and CRL displayed activity maxima (i.e., point for maximum catalytic activity across the temperature range) in copolymer brush mixtures (FIG. 1b,c), which suggest the existence of an optimal SBMA/OEGMA copolymer brush composition. In order to quantify the affinity of each lipase to the different copolymer brushes, an "activity weighted composition" ($\overline{C}_v$) was defined. The change of $\overline{C}_v$ across the temperature range was quantified for the different lipases (Supplemental FIG. S3), and it can be observed that at low temperatures, the activity weighted composition of all the lipases corresponds to a value of around 50% OEGMA, which hints that there is not a noticeable difference in the stability of lipases in environments of varied hydrophilicity. Nevertheless, as temperature is increased in the activity measurements, the lipases differentiate their behavior by displaying larger activity values in some copolymer brush compositions than in others, which leads to a change of $\overline{C}_v$ towards the composition in which the displayed catalytic activity is maximal. For instance, BSLA, which shows the most affinity to pure SBMA brushes (i.e., more affinity to hydrophilic environments) begins with a $\overline{C}_v$ of 50% OEGMA and leans towards a composition of 0% OEGMA as temperature increases, whereas CALB leans from 50% OEGMA towards 100% OEGMA as the temperature increases. Once again, RML and CRL show milder copolymer mixture preferences, although RML ends up resulting in a preference for SBMA brushes, whereas CRL remains stable at the 50% OEGMA concentration across the whole range of the temperature activity profile. This evolution of $\overline{C}_v$ by increasing the measurement temperature can be explained by the fact that the enzymes reveal their copolymer mixture preference when their stability is challenged at denaturing conditions such as high temperatures, whereas not so much when protein stability is not compromised. Further, among all the $\overline{C}_v$ profiles at different temperatures, each had an assigned optimal catalytic temperature ($T_{opt}$), and the corresponding $\overline{C}_v$ at $T_{opt}$, which were of 12%, 28%, 47% and 100% for BSLA, RML, CRL and CALB, respectively.

Example 6—Lipases' Surface Heterogeneity Matching with Optimal Copolymer Brush Composition In order to elucidate the aspects about lipase surface heterogeneity that may determine the preferential stabilization on different random copolymer brushes grafted from silica surfaces at $T_{opt}$, results from the hi-patch script (Table 1) were analyzed. Plausible correlations with the polymer brush composition—which indirectly incorporate a wide range of hydrophilicity/hydrophobicity at the nanoscale—were investigated. Intuitively, fractional hydrophobic coverage of the protein surfaces could be a reasonable proxy for the trend of the differential preference of the variety of lipases on the plethora of surfaces, nevertheless, it seemed to display no apparent consistent correlation for the four enzymes considered in this study. Interestingly, considering the specific hydrophobic intensity of the hydrophobic patches on the protein surface (summed $\Delta G^{solv}$ per patch area of all the protein), seemed to have a reasonable correlation with $\overline{C}_v$ at the $T_{opt}$ for each lipase, but most importantly, considering both the hydrophilic and hydrophobic contributions ($\Delta G^{solv}$ per area of the whole protein surface) yielded an enhanced correlation with respect to $\overline{C}_v$ at the $T_{opt}$ (FIG. 5). This could be explained by the fact regions belonging to hydrophobic patches roughly correspond to 20-25% of the total surface of these lipases, therefore, considering just the hydrophobic contribution from the patches would not capture the entirety of interactions of the protein surface with the solvent and the copolymer brushes. Moreover, given the dynamic nature of the polymer brushes, we hypothesize that non-patch-belonging regions from the protein surface also play a major role in the interaction with the brushes, and specially, SBMA monomers. Possibly, the study of just different HPs, as well as their hydrophobic intensity and distribution, could constitute a key approach to understand the role of hydrophobicity on protein aggregation, multimer formation, molecule binding and binding on stationary surfaces; whereas in the interaction with solvents and surfaces of dynamic nature such as polymer brush coated surfaces or polymer-protein conjugates, with the ability to self-assemble on the protein surface, whole-surface approaches appear to be more convenient to capture the ensemble of interactions with the inherently heterogeneous nature of proteins. Interestingly, the results from the hi-patch script appear to outrank the hydrophobic score of the established hpatch tool for hydrophobic patch detection and protein hydrophobicity ranking (Table 2). Indeed, the whole-protein values of $\Delta G^{solv}$/area were proven to correlate substantially better than the hpatch score with the $\overline{C}_v$ at the $T_{opt}$ for the different lipases that were studied.

REFERENCES (1) Schmid, A.; Dordick, J. S.; Hauer, B.; Kiener, A.; Wubbolt, M.; Witholt, B. Industrial Biocatalysis Today and Tomorrow. Nature 2001, 409 (January), 258-268.

(2) Campos, K. R.; Coleman, P. J.; Alvarez, J. C.; Dreher, S. D.; Garbaccio, R. M.; Terrett, N. K.; Tillyer, R. D.;

Truppo, M. D.; Parmee, E. R. The Importance of Synthetic Chemistry in the Pharmaceutical Industry. Science (80-.). 2019, 363 (6424).

(3) Bornscheuer, U. T.; Huisman, G. W.; Kazlauskas, R. J.; Lutz, S.; Moore, J. C.; Robins, K. Engineering the Third Wave of Biocatalysis. Nature 2012, 485 (7397), 185-194.

(4) Taverna, D. M.; Goldstein, R. A. Why Are Proteins Marginally Stable? Proteins Struct. Funct. Genet. 2002, 46 (1), 105-109. https://doi.org/10.1002/prot.10016.

(5) Adams, M. W. W.; Perler, F. B.; Kelly, R. M. Extremozymes: Expanding the Limits of Biocatalysis. Nature Biotechnology. 1995, pp 662-668.

(6) Haki, G. D.; Rakshit, S. K. Developments in Industrially Important Thermostable Enzymes: A Review. Bioresour. Technol. 2003, 89 (1), 17-34.

(7) Devine, P. N.; Howard, R. M.; Kumar, R.; Thompson, M. P.; Truppo, M. D.; Turner, N. J. Extending the Application of Biocatalysis to Meet the Challenges of Drug Development. Nat. Rev. Chem. 2018, 2 (12), 409-421.

(8) Cao, L. Immobilised Enzymes: Science or Art? Cliff. Opin. Chem. Biol. 2005, 9 (2), 217-226.

(9) Datta, S.; Christena, L. R.; Rajaram, Y. R. S. Enzyme Immobilization: An Overview on Techniques and Support Materials. 3 Biotech 2013, 3 (1), 1-9.

(10) Klibanov, A. M. Enzyme Stabilization by Immobilization. Anal. Biochem. 1979, 93, 1-25.

(11) Barbosa, O.; Torres, R.; Ortiz, C.; Berenguer-Murcia, A.; Rodrigues, R. C.; Fernandez-Lafuente, R. Heterofunctional Supports in Enzyme Immobilization: From Traditional Immobilization Protocols to Opportunities in Tuning Enzyme Properties. Biomacromolecules 2013, 14 (8), 2433-2462.

(12) Barbosa, O.; Ortiz, C.; Berenguer-Murcia, A.; Torres, R.; Rodrigues, R. C.; Fernandez-Lafuente, R. Strategies for the One-Step Immobilization-Purification of Enzymes as Industrial Biocatalysts. Biotechnol. Adv. 2015, 33 (5), 435-456.

(13) Rodrigues, R. C.; Ortiz, C.; Berenguer-Murcia, A.; Torres, R.; Fernandez-Lafuente, R. Modifying Enzyme Activity and Selectivity by Immobilization. Chem. Soc. Rev. 2013, 42 (15), 6290-6307.

(14) Brittain, W. J.; Minko, S. A Structural Definition of Polymer Brushes. J. Polym. Sci. Part A Polym. Chem. 2007, 45 (16), 3505-3512.

(15) Cullen, S. P.; Liu, X.; Mandel, I. C.; Himpsel, F. J.; Gopalan, P. Polymerie Brushes as Functional Templates for Immobilizing Ribonuclease A: Study of Binding Kinetics and Activity. Langmuir 2008, 24 (3), 913-920.

(16) Zoppe, J. O.; Ataman, N. C.; Mocny, P.; Wang, J.; Moraes, J.; Klok, H. A. Surface Initiated Controlled Radical Polymerization: State-of-the-Art, Opportunities, and Challenges in Surface and Interface Engineering with Polymer Brushes. Chem. Rev. 2017, 117 (3), 1105-1318.

(17) Zoppe, J. O.; Ataman, N. C.; Mocny, P.; Wang, J.; Moraes, J.; Klok, H. A. Surface-Initiated Controlled Radical Polymerization: State-of-the-Art, Opportunities, and Challenges in Surface and Interface Engineering with Polymer Brushes. Chem. Rev. 2017, 117 (3), 1105-1318.

(18) Xu, F. J.; Neoh, K. G.; Kang, E. T. Bioactive Surfaces and Biomaterials via Atom Transfer Radical Polymerization. Prog. Polym. Sci. 2009, 34 (8), 719-761.

(19) Xu, F. J.; Cai, Q. J.; Li, Y. L.; Kang, E. T.; Neoh, K. G. Covalent Immobilization of Glucose Oxidase on Well-Defined Poly(Glycidyl Methacrylate)-Si(111) Hybrids from Surface-Initiated Atom-Transfer Radical Polymerization. Biomacromolecules 2005, 6 (2), 1012-1020.

(20) Weltz, J. S.; Kienle, D. F.; Schwartz, D. K.; Kaar, J. L. Dramatic Increase in Catalytic Performance of Immobilized Lipases by Their Stabilization on Polymer Brush Supports. ACS Catal. 2019, 4992-5001.

(21) Palomo, J. M.; Segura, R. L.; Fernandez-Lorente, G.; Pernas, M.; Rua, M. L.; Guisan, J. M.; Fernandez-Lafuente, R. Purification, Immobilization, and Stabilization of a Lipase from Bacillus Thermocatenulatus by Interfacial Adsorption on Hydrophobic Supports. Biotechnol. Prog. 2004, 20 (2), 630-635.

(22) Fernandez-Lorente, G.; Terreni, M.; Mateo, C.; Bastida, A.; Fernandez-Lafuente, R.; Dalmases, P.; Huguet, J.; Guisan, J. M. Modulation of Lipase Properties in Macro-Aqueous Systems by Controlled Enzyme Immobilization: Enantioselective Hydrolysis of a Chiral Ester by Immobilized Pseudomonas Lipase. Enzyme Microb. Technol. 2001, 28 (4-5), 389-396.

(23) Scouten, W. H.; Luong, J. H. T.; Stephen Brown, R. Enzyme or Protein Immobilization Techniques for Applications in Biosensor Design. Trends Biotechnol. 1995, 13 (5), 178-185.

(24) Hartono, S. B.; Qiao, S. Z.; Liu, J.; Jack, K.; Ladewig, B. P.; Hao, Z.; Lu, G. Q. M. Functionalized Mesoporous Silica with Very Large Pores for Cellulase Immobilization. J. Phys. Chem. C 2010, 114 (18), 8353-8362.

(25) Qi, H.; Du, Y.; Hu, G.; Zhang, L. Poly(Carboxybetaine Methacrylate)-Functionalized Magnetic Composite Particles: A Biofriendly Support for Lipase Immobilization. Int. J. Biol. Macromol. 2018, 107, 2660-2666.

(26) Weltz, J. S.; Kienle, D. F.; Schwartz, D. K.; Kaar, J. L. Reduced Enzyme Dynamics upon Multipoint Covalent Immobilization Leads to Stability-Activity Trade-Off. J. Am. Chem. Soc. 2020.

(27) Iyer, P. V.; Ananthanarayan, L. Enzyme Stability and Stabilization-Aqueous and Non-Aqueous Environment. Process Biochem. 2008, 43 (10), 1019-1032.

(28) Jacak, R.; Leaver-Fay, A.; Kuhlman, B. Computational Protein Design with Explicit Consideration of Surface Hydrophobic Patches. Proteins Struct. Funct. Bioinforma. 2012, 80 (3), 825-838.

GLOSSARY OF CLAIM TERMS

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "composition" is intended to encompass a product comprising the specified ingredients in the specified amounts, as well as any product which results, directly or indirectly, from combination of the specified ingredients in the specified amounts. A polymer is a chemical compound or mixture of compounds formed by polymerization and consisting essentially of repeating structural units (e.g., a monomer). A monomer is a molecule that can be bonded to other identical molecules to form a polymer. A homopolymer is a polymer that is made up of only one type of monomer unit. A copolymer is a polymer formed when two (or more) different types of monomers are linked in the same polymer chain (as opposed to a homopolymer where only one monomer is used). A statistical copolymer is a polymer in which two or more monomers are arranged in a sequence that follows some statistical rule. If the mole fraction of a monomer be equal to the probability of finding a residue of that monomer at any point in the chain, the polymer is a random polymer. These polymers are generally synthesized via the free radical polymerization method.

As used herein, the term "base material" refers to a substrate providing one or more surfaces, where the surface is capable of forming polymer brushes, or to which polymer brushes can be grafted or otherwise affixed.

As used herein, the term "brush" or "polymer brush" refers to a polymeric side chain that is formed from a polymerization substrate having a radical-polymerizable terminal group, wherein the polymerizable substrate is the base material, or can be engrafted to or otherwise affixed to the base material, thereby substantially taking the form of the base material.

As used herein the term "reactive monomer" refers to a compound that is capable of participating in a radical induced grafting reaction. The reactive monomer can be any material capable of forming polymers as described above and herein, for example but not limited to glycidyl methacrylate (GMA), or ethylene. The base material and reactive monomer may be of the same compound, for example, a polyethylene base material may utilize ethylene monomers or polymers in the grafting reaction.

Kits for practicing the methods of the invention are further provided. By "kit" is intended any manufacture (e.g., a package or a container) comprising at least one reagent, e.g., a polymerization precursor mixture of the invention. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described, providing a monomer-containing polymerization precursor mixture, wherein the monomer mixture comprises a hydrophilic monomer and a hydrophobic monomer in a molar ratio between 100:1 and 1:100 of hydrophilic monomer: hydrophobic monomer, wherein the hydrophilic monomer is selected from the group consisting of [3-(methacryloylamino)propyl]trimethylammonium chloride, [2-(methacryloyloxy)ethyl]trimethylammonium chloride, 3-sulfopropyl methacrylate, [2-(methacryloyloxy)ethyl]dimethyl-(3-sulfopropyl)ammonium hydroxide, methacrylic acid, 2-methacryloyloxyethyl phosphorylcholine, and corresponding acrylates and acrylamides thereof and wherein the hydrophobic monomer is a monomer selected from the group consisting of poly(ethylene glycol)methacrylate benzyl methacrylate, cyclohexyl methacrylate, 2-(diethylamino)ethyl methacrylate, 2-(diisopropylamino)ethyl methacrylate, n-isopropylacrylamide, 2-N-Morpholinoethyl methacrylate, and corresponding acrylates and acrylamides thereof;

performing a polymerization reaction with the precursor mixture in the presence of a substrate surface to yield a polymerized substrate comprising a copolymer brush; and contacting the polymerized substrate with an enzyme under conditions effective to allow for attachment of the enzyme to the copolymer brush of the polymerized substrate.

2. The method of preparing an immobilized enzyme according to claim 1 wherein the molar ratio of hydrophilic monomer: hydrophobic monomer is selected based upon the protein surface hydrophilicity, wherein a greater protein surface hydophilicity mandates a higher ratio of hydrophilic monomer to hydrophobic monomer in the copolymer.

3. The method of preparing an immobilized enzyme according to claim 1 wherein the monomer mixture further commprises a reactive monomer.

TABLE 1

| Output from the hi-patch script for BSLA, RML, CRL and CALB. | | | | | |
|---|---|---|---|---|---|
| Protein | # patches | Total surface (nm$^2$) | % hydrophobic coverage | DG$^{solv}$ (kJ/mol) | DG$^{solv}$ per area (J/mol-Å$^2$) |
| Bacilus subtilis Lipase A (BSLA) | 19 | 80.3 | 21.83 | −1.36 | −16.7 |
| Rhizomucor miehei lipase (RML) | 23 | 107.4 | 20.91 | −1.60 | −14.9 |
| Candida Rugosa Lipase (CRL) | 39 | 178.3 | 18.74 | −2.52 | −14.1 |
| Candida Antarctica Lipase B (CALB) | 25 | 121.7 | 24.32 | −0.924 | −7.59 |

TABLE 2

| Comparison of hpatch and hi-patch outputs with respect to $\overline{C}_v$ at the T$_{opt}$. | | | |
|---|---|---|---|
| Protein | ΔG$^{solv}$ per area (J/mol-Å$^2$) | hpatch score (a.u.) | $\overline{C}_v$ at the T$_{opt}$ (% OEGMA) |
| BSLA | −16.7 | 26.72 | 12.58 ± 0.64 |
| RML | −14.9 | 47.52 | 27.76 ± 5.03 |
| CRL | −14.1 | 24.32 | 46.92 ± 2.89 |
| CALB | −7.59 | 68.32 | 100 ± 0 |

What is claimed is:

1. A method of preparing an immobilized enzyme comprising the steps of

4. The method of preparing an immobilized enzyme according to claim 3 wherein the reactive monomer is a monomer selected from the group consisting of glycidyl methacrylate and corresponding acrylates and acrylamides, nitrilotriacetic acid and iminodiacetic acid functionalized monomers.

5. The method of preparing an immobilized enzyme according to claim 1 wherein the precursor mixture includes an amine reactive cross-linking agent.

6. The method of preparing an immobilized enzyme according to claim 5 wherein the amine reactive cross-linking agent is methacrylic acid N-hydroxysuccinimide ester (NHS-MA).

7. The method of preparing an immobilized enzyme according to claim 1 wherein the copolymer brush is synthesized using a "grafted from" approach.

8. The method of preparing an immobilized enzyme according to claim 1 wherein the molar ratio hydrophilic monomer: hydrophobic monomer is a ratio selected from the group consisting of about 20:1, about 15:1, about 12:1, about 10:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:10, about 1:12, about 1:15, and about 1:20.

9. The method of preparing an immobilized enzyme according to claim 1 wherein the substrate surface is a silica surface.

10. The method of preparing an immobilized enzyme according to claim 1 wherein the substrate is a microsphere.

* * * * *